(12) United States Patent
Bazinet et al.

(10) Patent No.: US 9,533,003 B2
(45) Date of Patent: Jan. 3, 2017

(54) METHODS FOR THE TREATMENT OF HEPATITIS B AND HEPATITIS D INFECTIONS

(71) Applicant: Replicor Inc, Montreal (CA)

(72) Inventors: Michel Bazinet, Montreal (CA); Andrew Vaillant, Roxboro (CA)

(73) Assignee: REPLICOR INC., Montreal QC (CA)

( * ) Notice: Subject to any disclaimer, the term of this patent is extended or adjusted under 35 U.S.C. 154(b) by 0 days.

(21) Appl. No.: 14/854,200

(22) Filed: Sep. 15, 2015

(65) Prior Publication Data

US 2016/0263143 A1    Sep. 15, 2016

Related U.S. Application Data

(62) Division of application No. 14/449,173, filed on Aug. 1, 2014, now Pat. No. 9,200,283, which is a division of application No. 13/896,421, filed on May 17, 2013, now Pat. No. 9,133,458.

(60) Provisional application No. 61/703,816, filed on Sep. 21, 2012, provisional application No. 61/695,040, filed on Aug. 30, 2012.

(51) Int. Cl.

| | | |
|---|---|---|
| *A61K 31/7105* | (2006.01) | |
| *A61K 45/06* | (2006.01) | |
| *A61K 47/48* | (2006.01) | |
| *A61K 38/21* | (2006.01) | |
| *A61K 38/22* | (2006.01) | |
| *A61K 39/42* | (2006.01) | |
| *A61K 31/519* | (2006.01) | |
| *A61K 31/7088* | (2006.01) | |
| *A61K 31/566* | (2006.01) | |
| *A61K 31/713* | (2006.01) | |
| *C12N 15/113* | (2010.01) | |

(52) U.S. Cl.
CPC ......... *A61K 31/7105* (2013.01); *A61K 31/519* (2013.01); *A61K 31/566* (2013.01); *A61K 31/7088* (2013.01); *A61K 31/713* (2013.01); *A61K 38/212* (2013.01); *A61K 38/215* (2013.01); *A61K 38/217* (2013.01); *A61K 38/2292* (2013.01); *A61K 39/42* (2013.01); *A61K 45/06* (2013.01); *A61K 47/48215* (2013.01); *C12N 15/1131* (2013.01)

(58) Field of Classification Search
None
See application file for complete search history.

(56) References Cited

U.S. PATENT DOCUMENTS

| | | |
|---|---|---|
| 8,008,269 B2 | 8/2011 | Vaillant et al. |
| 8,008,270 B2 | 8/2011 | Vaillant et al. |
| 8,067,385 B2 | 11/2011 | Vaillant et al. |
| 8,350,021 B2 | 1/2013 | Pachuk et al. |
| 8,809,293 B2 | 8/2014 | Chin et al. |
| 9,133,458 B2 | 9/2015 | Bazinet et al. |
| 2003/0206887 A1 | 11/2003 | Morrissey et al. |
| 2004/0054156 A1 | 3/2004 | Draper et al. |
| 2004/0127446 A1 | 7/2004 | Blatt et al. |
| 2004/0162253 A1 | 8/2004 | Vaillant et al. |
| 2006/0135458 A1* | 6/2006 | Vaillant .............. A61K 31/7088 514/44 A |
| 2007/0027099 A1 | 2/2007 | Lin et al. |
| 2012/0046348 A1 | 2/2012 | Vaillant et al. |
| 2013/0309201 A1 | 11/2013 | Bazinet et al. |
| 2013/0310445 A1 | 11/2013 | Bazinet et al. |
| 2014/0369962 A1 | 12/2014 | Bazinet et al. |
| 2014/0369963 A1 | 12/2014 | Bazinet et al. |

FOREIGN PATENT DOCUMENTS

| | | |
|---|---|---|
| CA | 2254931 | 12/1997 |
| CA | 2405502 | 10/2001 |
| WO | 0172294 | 10/2001 |
| WO | 2011047316 | 4/2011 |
| WO | 2012021985 | 2/2012 |
| WO | 2012047856 | 4/2012 |
| WO | 2013/003520 | 1/2013 |

OTHER PUBLICATIONS

Klein et al., 2003, Gastroenterology, 125: 9-18.
Arrowhead Research Corporation web site reprint of Pipeline section, May 21, 2015.
The RNAi Therapeutics blog, Apr. 23, 2015, "Absolute HBsAg levels, not percent decline may be goal of HBV RNAi".
Arrowhead Research, 3Q Fiscal 2014 conference call-prepared remarks, Aug. 12, 2014.
Cheng et al., 2005, Journal of hepatology, 43: 465-471.
Vanlandschoot et al., 2002, The Journal of general virology, 83: 1281-1289.
Wu et al., 2009, Hepatology, 49: 1132-1140.
Xu et al., 2009, Molecular immunology, 46: 2640-2646.
Wu et al. 2012 J. Inf. Dis. 206: 415-420.
Lang et al. 2011 J. Hepatol. 55: 762-769.
Gruffaz et al. 2013, J. Hepatol. 58 (supp1), p. s155, Abstract 378.
Kandimalla et al. 2011. Cell. Immunol. 270: 126-134.
Struthers et al. 2010. Cell. Immunol. 263: 105-113.
Bernstein et al., 2008, Antimicrobial Agents and Chemotherapy, 52: 2727-2733.
Cardin et al., 2009, Virology Journal, 6: 214.
Guzman et al., 2007, Antiviral Therapy, 12: 1147-1156.
Lee et al., 2008, Virology, 372: 107-117.
Matsumura et al., 2009, Gastroenterology, 137: 673-681.
Vaillant et al., 2006, Antimicrobial Agents and Chemotherapy, 50: 1393-1401.
Fu et al., 2008, Acta Pharmacol. Sin. 29: 1522-1528.
Hean et al., 2010, Artificial DNA: PNA & XNA, 1: 17-26.

(Continued)

*Primary Examiner* — Brian J Gangle
*Assistant Examiner* — Andrea McCollum
(74) *Attorney, Agent, or Firm* — Norton Rose Fulbright Canada LLP

(57) ABSTRACT

It is disclosed a method for the treatment of hepatitis B (HBV) infection or HBV/hepatitis D (HDV) co-infection, the method comprising administering to a subject in need of treatment a first pharmaceutically acceptable agent that removes the hepatitis B surface antigen from the blood and a second pharmaceutically acceptable agent which stimulates immune function.

13 Claims, 1 Drawing Sheet

(56) References Cited

OTHER PUBLICATIONS

Xin et al., 2008, World J. Gastroenterol., 14: 3849-3854.
Zhe et al., 2005, J. Zhejiang Univ. Sci., 6B: 236-241.
Chen et al., 2008, Pharmaceutical Res., 25: 72-86.
Sun et al., 2011, Biochem. Biophys. Res. Comm., 409: 430-435.
Muir et al., 2010, Hepatology, 52: 822-832.
Zhang et al., 2010, BMC Microbiol. 10:214.
Starkey et al., 2009, J. Gen Virol. 90: 115-126.
Waters et al. 2011 Blood 117: 5514-5522.
Wlotzka et al. 2002 Proc. Nat. Acad. Sci. U.S.A. 99: 8898-8902.
Akdim et al. 2010 Journal of the Americal College of Cardiology 55: 1611-1618.
Riecke et al. 2012 Abstract 2432 presented at the 54th Annual ASH Meeting and Exposition, Atlanta, GA, U.S.A.
Patient et al., 2007, J. Virology 81: 3842-3851.
Moucari et al., 2009, Antiviral Ther., 14: 1183-1188.
Reijnders et al., 2011, J. Hepatol., 54: 449-454.
Moucari et al., 2009, Hepatology, 49: 1151-1157.
Karayiannis et al., 1990, J. Hepatol., 10: 350-352.
Friborg et al., 2013, Antimicrobial Agents and Chemotherapy, 57: 1312-1322.
Lau et al. 1991, Hepatology 14: 975-979.
McClary et al. 2000. Journal of Virology 74: 2255-2264.
Robek et al. 2005. Journal of Virology 79: 3851-3854.
Wu et al., 2007, Hepatology, 46: 1769-1778.
Horscroft et al., 2012, J. Antimicrob. Chemotherapy, 67: 789-801.
Lanford et al. 2013 Gastroenterology Feb. 12 in press; www.natap.org/2010/AASLD/AASLD_39.htm.
Yang et al., 2008, Antiviral Res. 77: 136-141.
Danenberg et al., 1995, Vaccine, 13: 1445-1448.
Khorram et al., 1997, J. Gerontol. A. Biol. Sci. Med. Sci., 52: M1-M7.
Woltman et al., 2011, PloS One 6: e15324.
Loria, 2002, Steroids, 67: 953-966.
Carmona et al., 2009, Molecular Pharmaceutics, 6 : 706-717.
Giladi et al., 2003, Molecular Therapy, 8: 769-776.
Peng et al., 2005, J Gen Virol, 86: 3227-3234.
Morrissey et al., 2005, Nature Biotechnology, 23: 1002-1007.
Chen and Mahato, 2008, J Drug Target., 16: 140-148.
Meng et al., 2008, Journal of Virological Methods, 150: 27-33.
Arrowhead Research Corporation Open Letter of Oct. 9, 2014.
Knoferl et al., 2003, J. Appl. Physiol., 95: 529-535.
Oberbeck et al., 2007, Inten. Car Med., 33: 2207-2213.
Burdick et al., 2009, Int. Immunopharmacol., 9: 1342-1346.
Hazeldine et al., 2010, J. Steroid Biochem. Mol. Biol., 120: 127-136.
Araeno et al., 1993, J. Inf. Dis., 167: 830-840.
Liang et al. 2011. Virology Journal 8: 69.
Mahtab et al. 2013. J. Hepatol. 58 (supp 1) abstract 776.
Aagaard et al. 2007, Advanced Drug Delivery Reviews 59:75-86.
Warzocha et al. Leukemia and Lymphoma vol. 24: 267-281.
Mahtab et al., 2011, Hepatology, 54(S1), Abstract 235, pp. 478A-479A.
Yu et al., 2011, Journal of Medicinal Chemistry, 54: 5660-5670.
Menne et al., 2002, Journal of Virology, 76(11): 5305-5314.
Op Den Brouw et al., 2008, Immunology, 126: 280-289.
Chen et al., 2012, Journal of Gastroenterology and Hepatology, 27(3): 481-486.
Wiegand et al., 2011, Z Gastroenterol., 49: 1463-1469.
Brunetto et al., 2009, Hepatology, 49(4): 1141-1150.
Al-Mahtab et al., 2013, journal of Hepatology, 58(S1), Abstract 776, p. S316.
Mahtab et al., 2012, Hepatology, 56(S1), Abstract 424, p. 401A.
Kulkarni et al., 2007, J. Am. Soc. Nephrol. 18: 2350-2358.
Schwoebel et al., 2013, Blood 121: 2311-2315.
Rinaldi et al., 2012, Br. J. Clin. Pharmacol. 74: 940-946.
Raal et al., 2010, Lancet 375: 998-1006.
Frank-Kemenetsky et al., 2008, Proc. Natl. Acad. Sci. 105: 11915-11920.
Janssen et al., 2013, New Eng. J. Med. 368: 1685-1694.
Goemans et al., 2011, New. Eng. J. Med. 364: 1513-1522.
Cirak et al., 2011, Mol. Therapy 20: 462-467.
Chan et al., 2012, poster 016, OTS meeting Boston, U.S.A.
Arrowhead Whitepaper 2012, www.arrowheadresearch.com/sites/default/files/press_releases/pdf/whitepaper-hbv-3-7-12.pdf.
Arrowhead ARC-520 press release Mar. 25, 2013, www.arrowheadresearch.com/press-releases/arrowhead-research-advances-arc-520-ind-enabling-studies-treatment-hepatitis-b.
Wooddell et al., 2013, Molecular Therapy, 21: 973-985.

\* cited by examiner 7-(2-chloro-6-fluorophenyl)-5-(4-chlorophenyl)-4,5,6,7-tetrahydro[1,2,4]triazolo[1,5-a]pyrimidine 5-(4-chlorophenyl)-7-(2,6-difluorophenyl)-4,7-dihydro[1,2,4]triazolo[1,5-a]pyrimidine ations Ser. No. 61/695,040, filed Aug. 30, 2012, and from U.S. Provisional Application Ser. No. 61/703,816 filed Sep. 21, 2012, the entire content of which are incorporated herein by reference.

SEQUENCE LISTING

```
<160> NUMBER OF SEQ ID NOS: 20

<210> SEQ ID NO 1
<211> LENGTH: 40
<212> TYPE: DNA
<213> ORGANISM: Artificial Sequence
<220> FEATURE:
<223> OTHER INFORMATION: fully phosphorothioated

<400> SEQUENCE: 1
cacacacaca cacacacaca cacacacaca cacacacaca                           40

<210> SEQ ID NO 2
<211> LENGTH: 40
<212> TYPE: DNA
<213> ORGANISM: Artificial Sequence
<220> FEATURE:
<223> OTHER INFORMATION: REP 2055, fully phosphorothioated

<400> SEQUENCE: 2
acacacacac acacacacac acacacacac acacacacac                           40

<210> SEQ ID NO 3
<211> LENGTH: 40
<212> TYPE: DNA
<213> ORGANISM: Artificial Sequence
<220> FEATURE:
<223> OTHER INFORMATION: REP 2148, fullly phosphorothioated, C = 5'
      methylcytidine

<400> SEQUENCE: 3
acacacacac acacacacac acacacacac acacacacac                           40

<210> SEQ ID NO 4
<211> LENGTH: 40
```

```
<212> TYPE: DNA
<213> ORGANISM: Artificial Sequence
<220> FEATURE:
<223> OTHER INFORMATION: fully phosphorothioated, C = 5' methylcytidine

<400> SEQUENCE: 4
cacacacaca cacacacaca cacacacaca cacacacaca                    40

<210> SEQ ID NO 5
<211> LENGTH: 40
<212> TYPE: RNA
<213> ORGANISM: Artificial Sequence
<220> FEATURE:
<223> OTHER INFORMATION: REP 2153, fully phosphorothioated, fully 2' O
      methylribose modified

<400> SEQUENCE: 5
acacacacac acacacacac acacacacac acacacacac                    40

<210> SEQ ID NO 6
<211> LENGTH: 40
<212> TYPE: RNA
<213> ORGANISM: Artificial Sequence
<220> FEATURE:
<223> OTHER INFORMATION: fully phosphorothioated, fully 2' O
      methylribose modified

<400> SEQUENCE: 6
cacacacaca cacacacaca cacacacaca cacacacaca                    40

<210> SEQ ID NO 7
<211> LENGTH: 40
<212> TYPE: DNA
<213> ORGANISM: Artificial Sequence
<220> FEATURE:
<223> OTHER INFORMATION: REP 2033, fully phosphorothioated

<400> SEQUENCE: 7
tgtgtgtgtg tgtgtgtgtg tgtgtgtgtg tgtgtgtgtg                    40

<210> SEQ ID NO 8
<211> LENGTH: 40
<212> TYPE: DNA
<213> ORGANISM: Artificial Sequence
<220> FEATURE:
<223> OTHER INFORMATION: fully phosphorothioated

<400> SEQUENCE: 8
gtgtgtgtgt gtgtgtgtgt gtgtgtgtgt gtgtgtgtgt                    40

<210> SEQ ID NO 9
<211> LENGTH: 40
<212> TYPE: RNA
<213> ORGANISM: Artificial Sequence
<220> FEATURE:
<223> OTHER INFORMATION: fully phosphorothioated, fully 2' O
      methylribose modifed, each cytosine 5' methylated

<400> SEQUENCE: 9
cacacacaca cacacacaca cacacacaca cacacacaca                    40

<210> SEQ ID NO 10
<211> LENGTH: 40
<212> TYPE: RNA
<213> ORGANISM: Artificial Sequence
<220> FEATURE:
<223> OTHER INFORMATION: REP 2139, fully phosphorothioated, fully 2' O
``` methylribose modified, each cytosine 5' methylated

<400> SEQUENCE: 10
acacacacac acacacacac acacacacac acacacacac                    40

<210> SEQ ID NO 11
<211> LENGTH: 40
<212> TYPE: DNA
<213> ORGANISM: Artificial Sequence
<220> FEATURE:
<223> OTHER INFORMATION: REP 2163, fully phosphorothioated, each
      cytosine 5' methylated
<220> FEATURE:
<221> NAME/KEY: misc_feature
<222> LOCATION: 1,3,5,7,9,11,13,15,17,19,21,23,25,27,29,31,33,35,
      37,39
<223> OTHER INFORMATION: 2' O methylribose modification

<400> SEQUENCE: 11
acacacacac acacacacac acacacacac acacacacac                    40

<210> SEQ ID NO 12
<211> LENGTH: 40
<212> TYPE: RNA
<213> ORGANISM: Artificial Sequence
<220> FEATURE:
<223> OTHER INFORMATION: REP 2164, fully phosphorothioated, each
      cytosine 5' methylated
<220> FEATURE:
<221> NAME/KEY: misc_feature
<222> LOCATION: 1-12, 14-26, 28-40
<223> OTHER INFORMATION: 2' O methylribose modification

<400> SEQUENCE: 12
acacacacac acacacacac acacacacac acacacacac                    40

<210> SEQ ID NO 13
<211> LENGTH: 40
<212> TYPE: RNA
<213> ORGANISM: Artificial Sequence
<220> FEATURE:
<223> OTHER INFORMATION: REP 2165, fully phosphorothioated, each
      cytosine 5' methylated
<220> FEATURE:
<221> NAME/KEY: misc_feature
<222> LOCATION: 1-10, 12-20, 22-30, 32-40
<223> OTHER INFORMATION: 2' O methylribose modification

<400> SEQUENCE: 13
acacacacac acacacacac acacacacac acacacacac                    40

<210> SEQ ID NO 14
<211> LENGTH: 40
<212> TYPE: RNA
<213> ORGANISM: Artificial Sequence
<220> FEATURE:
<223> OTHER INFORMATION: REP 2166, full phosphorothioated, each cytosine
      5' methylated and 2'O methylribose modified

<400> SEQUENCE: 14
acacacacac acacacacac acacacacac acacacacac                    40

<210> SEQ ID NO 15
<211> LENGTH: 40
<212> TYPE: DNA
<213> ORGANISM: Artificial Sequence
<220> FEATURE:
<223> OTHER INFORMATION: REP 2167, fully phosphorothioated, each
      cytosine 5' methylated

```
<220> FEATURE:
<221> NAME/KEY: misc_feature
<222> LOCATION: 2,4,6,8,10,12,14,16,18,20,22,24,26,28,30,32,34
      36,38,40
<223> OTHER INFORMATION: 2' O methyribose modification

<400> SEQUENCE: 15
acacacacac acacacacac acacacacac acacacacac                              40

<210> SEQ ID NO 16
<211> LENGTH: 40
<212> TYPE: DNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 2,4,6,8,10,12,14,16,18,20,22,24,26,28,30,32,34
      36,38,40
<223> OTHER INFORMATION: 2' O methylribose modification

<400> SEQUENCE: 16
cacacacaca cacacacaca cacacacaca cacacacaca                              40

<210> SEQ ID NO 17
<211> LENGTH: 40
<212> TYPE: RNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1-13, 15-27, 29-40
<223> OTHER INFORMATION: 2' O methylribose modification

<400> SEQUENCE: 17
cacacacaca cacacacaca cacacacaca cacacacaca                              40

<210> SEQ ID NO 18
<211> LENGTH: 40
<212> TYPE: RNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1-9, 11-29, 21-29, 31-40
<223> OTHER INFORMATION: 2' O methylribose modification

<400> SEQUENCE: 18
cacacacaca cacacacaca cacacacaca cacacacaca                              40

<210> SEQ ID NO 19
<211> LENGTH: 40
<212> TYPE: RNA
<213> ORGANISM: Artificial Sequence
<220> FEATURE:
<223> OTHER INFORMATION: fully phosphorothioated, each cytosine
      5' methylated and 2'O methylribose modified

<400> SEQUENCE: 19
cacacacaca cacacacaca cacacacaca cacacacaca                              40

<210> SEQ ID NO 20
<211> LENGTH: 40
<212> TYPE: DNA
```

```
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1,3,5,7,9,11,13,15,17,19,21,23,25,27,29,31,33,35,
      37,39
<223> OTHER INFORMATION: 2' O methylribose modification

<400> SEQUENCE: 20
cacacacaca cacacacaca cacacacaca cacacacaca                    40
```

METHODS FOR THE TREATMENT OF HEPATITIS B AND HEPATITIS D INFECTIONS

CROSS REFERENCE TO RELATED APPLICATION

This application is a divisional of U.S. application Ser. No. 14/449,173 filed Aug. 1, 2014, which is a divisional of U.S. application Ser. No. 13/896,421 filed May 17, 2013, which claims priority from U.S. Provisional Application Ser. No. 61/695,040, filed Aug. 30, 2012, and from U.S. Provisional Application Ser. No. 61/703,816 filed Sep. 21, 2012, the entire content of which are incorporated herein by reference.

TECHNICAL FIELD

The present description relates to methods of treating a subject with hepatitis B infection or hepatitis B/hepatitis D virus co-infection with a treatment comprising a first pharmaceutically acceptable agent that removes the hepatitis B surface antigen from the blood and a second pharmaceutically acceptable immunotherapeutic agent that stimulates immune function.

BACKGROUND ART

The hepatitis B virus (HBV) afflicts 400 million individuals worldwide and causes an estimated 600,000 deaths each year from complications arising from HBV infection. While several antiviral treatments are approved for use, none of these is able to elicit a therapeutically effective immune response capable of providing durable control of infection except in a small fraction of patients undergoing treatment. As such, there exists a clear unmet medical need for a treatment regimen which can elicit a durable immunological control of HBV infection in a large proportion of patients receiving this treatment.

HBV infection results in the production of two different particles: 1) the HBV virus itself (or Dane particle) which includes a viral capsid assembled from the HBV core antigen protein (HBcAg) and is covered by the hepatitis B surface antigen (HBsAg) and is capable of reinfecting cells and 2) subviral particles (or SVPs) which are high density lipoprotein-like particles comprised of lipids, cholesterol, cholesterol esters and the small and medium forms of the hepatitis B surface antigen (HBsAg) which are non-infectious. For each viral particle produced, 1,000-10,000 SVPs are released into the blood. As such SVPs (and the HBsAg protein they carry) represent the overwhelming majority of viral protein in the blood. HBV infected cells also secrete a soluble proteolytic product of the pre-core protein called the HBV e-antigen (HBeAg).

The hepatitis D virus (HDV) uses HBsAg to form its viral structure (Taylor, 2006, Virology, 344: 71-76) and as such, HDV infection can only occur in subjects with concomitant HBV infection. While the incidence of HDV co-infection in asymptomatic HBV carriers and chronic HBV-related liver disease is low in countries with a low incidence of HBV infection, it is a significant complication in HBV-infected subjects in countries with a high incidence of HBV infection and can increase the rate of progression of liver disease to fulminant hepatitis. As such, the clear unmet medical need in HBV infection is even more pressing in HBV/HDV co-infected subjects.

The current standard methods of treatment for HBV include interferon- or thymosin α1-based immunotherapies and the suppression of viral production by inhibition of the HBV polymerase. HBV polymerase inhibitors are effective in reducing viral production but have little to no effect in rapidly reducing HBsAg or can slowly reduce HBsAg with long term treatment in a limited number of patients (as is the case with tenofovir disoproxil fumarate). Interferon based immunotherapy can achieve a reduction of both viral production and early removal of HBsAg from the blood but only in a small percentage of treated subjects. The generally accepted role of HBsAg in the blood is to sequester anti-HBsAg antibodies and allow infectious viral particles to escape immune detection which is likely one of the reasons why HBV infection remains a chronic condition. In addition HBsAg, HBeAg and HBcAg all have immuno-inhibitory properties as discussed below and the persistence of these viral proteins in the blood of patients following the administration of any of the currently available treatments for HBV as described above is likely having a significant impact in preventing patients from achieving immunological control of their HBV infection.

Although the three primary HBV proteins (HBsAg, HBeAg and HBcAg) all have immunoinhibitory properties (see below), HBsAg comprises the overwhelming majority of HBV protein in the circulation of HBV infected subjects. Additionally, while the removal (via seroconversion) of HBeAg or reductions in serum viremia are not correlated with the development of sustained control of HBV infection off treatment, the removal of serum HBsAg from the blood (and seroconversion) in HBV infection is a well-recognized excellent prognostic indicator of antiviral response on treatment which will lead to control of HBV infection off treatment (although this only occurs in a small fraction of patients receiving immunotherapy). Thus, while reduction of all three major HBV proteins (HBsAg, HBeAg and HBcAg) may result in the optimal removal of inhibitory effect, the removal of HBsAg alone is likely sufficient in and of itself to remove the bulk of the viral inhibition of immune function in subjects with HBV infection.

Therefore, in the absence of any current treatment regimen which can restore immunological control of HBV in a large proportion of patients, there is a need to be provided with an effective treatment against HBV infection and HBV/HDV co-infection which can restore immunological control in the majority of patients.

SUMMARY

In accordance with the present description there is now provided a method for the treatment of HBV infection or HBV/HDV co-infection in a subject requiring such treatment, the method comprising the administration of a first pharmaceutically acceptable agent which removes HBsAg from the blood of the HBV infected host and a second pharmaceutically acceptable immunotherapeutic agent that stimulates immune function.

There is also provided a method for the treatment of HBV infection or HBV/HDV co-infection in a subject requiring such treatment, the method comprising the administration of a first pharmaceutically acceptable agent which inhibits the release of HBsAg from infected cells and a second pharmaceutically acceptable immunotherapeutic agent which stimulates immune function.

There is also provided a method for the treatment of HBV infection or HBV/HDV co-infection in a subject requiring such treatment, the method comprising the administration of an effective dosing regimen of a first pharmaceutically acceptable agent which inhibits the release of HBV subviral particles from infected cells and an effective dosing regimen of a second pharmaceutically acceptable immunotherapeutic agent which stimulates immune function.

There is also provided a method for the treatment of HBV infection or HBV/HDV co-infection in a subject requiring such treatment, the method comprising the administration of a first pharmaceutically acceptable agent which inhibits the formation of HBV subviral particles in infected cells and a second pharmaceutically acceptable immunotherapeutic agent which stimulates immune function.

There is also provided a method for the treatment of HBV infection or HBV/HDV co-infection in a subject requiring such treatment, the method comprising the administration of a first pharmaceutically acceptable agent which inhibits the synthesis of or lowers the intracellular concentration of HBsAg in infected cells and a second pharmaceutically acceptable immunotherapeutic agent which stimulates immune function.

There is also provided a method for the treatment of HBV infection or HBV/HDV co-infection in a subject requiring such treatment, the method comprising the administration of the first and second pharmaceutically acceptable agents as described above in combination in a single pharmaceutical composition or in two different pharmaceutical compositions given by the same route of administration.

There is also a provided a method for the treatment of HBV infection or HBV/HDV co-infection in a subject requiring such treatment, the method comprising the administration of the first and second pharmaceutical agents as described above simultaneously in a patient, whether given by the same or different routes of administration.

In accordance with the present description there is now provided the use of a first pharmaceutically acceptable agent which removes hepatitis B surface antigen from the blood in combination with a second pharmaceutically acceptable immunotherapeutic agent that stimulates immune function for the treatment of hepatitis B infection or hepatitis B/hepatitis D co-infection.

There is also provided the use of a first pharmaceutically acceptable agent which inhibits the release of HBsAg from infected cells and a second pharmaceutically acceptable immunotherapeutic agent which stimulates immune function for the treatment of hepatitis B infection or hepatitis B/hepatitis D co-infection.

There is also provided the use of a first pharmaceutically acceptable agent which inhibits the release of HBV subviral particles from infected cells and a second pharmaceutically acceptable immunotherapeutic agent which stimulates immune function for the treatment of hepatitis B infection or hepatitis B/hepatitis D co-infection.

There is also provided the use of a first pharmaceutically acceptable agent which inhibits the formation of HBV subviral particles in infected cells and a second pharmaceutically acceptable immunotherapeutic agent which stimulates immune function for the treatment of hepatitis B infection or hepatitis B/hepatitis D co-infection.

There is also provided the use of a first pharmaceutically acceptable agent which inhibits the synthesis of or lowers the intracellular concentration of HBsAg in infected cells and a second pharmaceutically acceptable immunotherapeutic agent which stimulates immune function for the treatment of hepatitis B infection or hepatitis B/hepatitis D co-infection.

There is also provided the use of a first pharmaceutically acceptable agent which removes hepatitis B surface antigen from the blood in combination with a second pharmaceutically acceptable immunotherapeutic agent that stimulates immune function in the manufacture of a medicament for the treatment of hepatitis B infection or hepatitis B/hepatitis D co-infection.

In accordance with the present description there is now provided a composition for the treatment of hepatitis B infection or hepatitis B/hepatitis D co-infection, said composition comprising an effective dose of a first pharmaceutically acceptable agent which removes hepatitis B surface antigen from the blood and an effective dosing regimen of a second pharmaceutically acceptable immunotherapeutic agent that stimulates immune function.

In an embodiment, the agent removing hepatitis B surface antigen from the blood inhibits the formation of HBV subviral particles.

In another embodiment, the agent removing hepatitis B surface antigen from the blood inhibits the intracellular transit of HBV subviral particles.

In another embodiment, the agent removing hepatitis B surface antigen from the blood inhibits the release of HBV subviral particles into the blood.

In another embodiment, the agent removing hepatitis B surface antigen from the blood inhibits the release of hepatitis B surface antigen from the infected cell.

In another embodiment, the agent removing hepatitis B surface antigen from the blood inhibits the synthesis of HBsAg and or another viral protein.

In another embodiment, the agent removing hepatitis B surface antigen from the blood inhibits the synthesis or function of apolipoprotein H.

In another embodiment, the agent removing hepatitis B surface antigen from the blood is a small molecule.

In another embodiment, the agent removing hepatitis B surface antigen from the blood is a nucleic acid polymer comprising a phosphorothioated oligonucleotide from 20-120 nucleotides in length comprising repeats of the sequence AC.

In another embodiment, the agent removing hepatitis B surface antigen from the blood is nucleic acid polymer comprising a phosphorothioated oligonucleotide from 20-120 nucleotides in length comprising the repeats of the sequence CA.

In another embodiment, the agent removing hepatitis B surface antigen from the blood is a nucleic acid polymer comprising a phosphorothioated oligonucleotide from 20-120 nucleotides in length comprising the repeats of the sequence TG.

In another embodiment, the agent removing hepatitis B surface antigen from the blood is a nucleic acid polymer comprising a phosphorothioated oligonucleotide from 20-120 nucleotides in length comprising the repeats of the sequence GT.

In another embodiment, the nucleic acid polymer further comprises at least one 2' ribose modification.

In another embodiment, the nucleic acid polymer further comprises all riboses having a 2' modification.

In another embodiment, the nucleic acid polymer further comprises at least one 2'O methyl ribose modification.

In another embodiment, the nucleic acid polymer further comprises all riboses having the 2'O methyl modification.

In another embodiment, the nucleic acid polymer further comprises at least one 5'methylcytosine.

In another embodiment, the nucleic acid polymer further comprises all cytosines present as 5'methylcytosine.

In another embodiment, the nucleic acid polymer further comprises at least one 2' ribose modification and at least one 5' methylcytosine.

In another embodiment, the nucleic acid polymer further comprises all riboses having the 2'O methyl modification and all cytosines present as 5'methylcytosine.

In another embodiment, the agent removing hepatitis B surface antigen from the blood is an oligonucleotide selected from the group consisting of SEQ ID NOs: 1-10.

In another embodiment, the agent removing hepatitis B surface antigen from the blood is an oligonucleotide chelate complex comprising an oligonucleotide selected from the group consisting of SEQ ID NOs: 1-10.

In another embodiment, the agent removing hepatitis B surface antigen from the blood is an oligonucleotide consisting of SEQ ID NO: 2.

In another embodiment, the agent removing hepatitis B surface antigen from the blood is an oligonucleotide chelate complex comprising SEQ ID NO: 2.

In another embodiment, the agent removing hepatitis B surface antigen from the blood is an oligonucleotide consisting of SEQ ID NO: 3.

In another embodiment, the agent removing hepatitis B surface antigen from the blood is an oligonucleotide chelate complex comprising an oligonucleotide selected from the group consisting of SEQ ID NO: 3.

In another embodiment, the agent removing hepatitis B surface antigen from the blood is an oligonucleotide consisting of SEQ ID NO: 10.

In another embodiment, the agent removing hepatitis B surface antigen from the blood is an oligonucleotide chelate complex comprising an oligonucleotide selected from the group consisting of SEQ ID NO: 10.

In another embodiment, the agent removing hepatitis B surface antigen from the blood is an antisense oligonucleotide which targets any portion of any HBV mRNA.

In another embodiment, the agent removing hepatitis B surface antigen from the blood is an antisense oligonucleotide which targets any portion of the human apolipoprotein H mRNA.

In another embodiment, the agent removing hepatitis B surface antigen from the blood is a siRNA which targets any portion of any HBV mRNA.

In another embodiment, the agent removing hepatitis B surface antigen from the blood is a siRNA which targets any portion of the human apolipoprotein H mRNA.

In another embodiment, the agent removing hepatitis B surface antigen from the blood is a shRNA which targets any portion of any HBV mRNA or

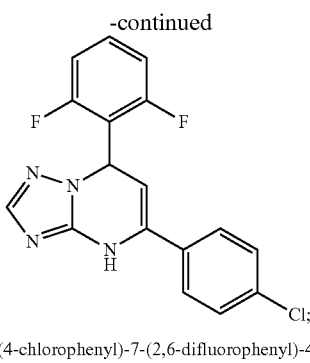

5-(4-chlorophenyl)-7-(2,6-difluorophenyl)-4,7-dihydro[1,2,4]triazolo[1,5-a]pyrimidine An oligonucleotide selected from the following:
SEQ ID NO: 2;
SEQ ID NO: 3;
SEQ ID NO: 10;
SEQ ID NOs: 1 and 4-9;
A nucleic acid polymer selected from the following:
   A phosphorothioated oligonucleotide from 20-120 nucleotides in length comprising repeats of the sequence AC;
   A phosphorothioated oligonucleotide from 20-120 nucleotides in length comprising repeats of the sequence CA;
   A phosphorothioated oligonucleotide from 20-120 nucleotides in length comprising repeats of the sequence TG and
   A phosphorothioated oligonucleotide from 20-120 nucleotides in length comprising repeats of the sequence GT;
An antisense oligonucleotide targeting any part of any HBV mRNA;
An antisense oligonucleotide targeting any part of the human apolipoprotein H mRNA;
A siRNA targeting any part of any HBV mRNA;
A siRNA targeting any part of the human apolipoprotein H mRNA;
A shRNA targeting any part of any HBV mRNA;
A shRNA targeting any part of the human apolipoprotein H mRNA;
A Speigelmer or aptamer targeting the hepatitis B surface antigen and
A Speigelmer or aptamer targeting human apoliporotein H;

and the second immunotherapeutic agent comprises one or more molecules from the group consisting of:
Thymosin α1;
Any α-interferon or pegylated derivatives thereof;
Any β-interferon or pegylated derivatives thereof;
Any γ-interferon or pegylated derivatives thereof;
Any λ-interferon or pegylated derivatives thereof;
Interferon α-2a or α-2b or α-N3;
Interferon β-1a or β-1b;
Interferon γ-1b;
Interferon λ1 or λ2 or λ3
Pegylated interferon α-2a or α-2b or λ1 or λ2;
Any antiviral cytokine or pegylated derivatives thereof;
Thymic protein A;
Any polypeptide shown to have antiviral activity or immunostimulatory activity;
An immunostimulatory oligonucleotide including IMO-2055 or IMO-2125;
A small molecule Toll-like receptor (TLR) agonist including GS-9620 or ANA-773; and
Any antiviral or immunostimulatory hormone including DHEA or its metabolites.

In a further embodiment, the following oligonucleotides can be further formulated as an oligonucleotide chelate complex:
SEQ ID NO: 2;
SEQ ID NO: 3;
SEQ ID NO 10;
SEQ ID NOs: 1 and 4-9;
A nucleic acid polymer selected from the following:
   A phosphorothioated oligonucleotide from 20-120 nucleotides in length comprising repeats of the sequence AC;
   A phosphorothioated oligonucleotide from 20-120 nucleotides in length comprising repeats of the sequence CA;
   A phosphorothioated oligonucleotide from 20-120 nucleotides in length comprising repeats of the sequence TG; and
   A phosphorothioated oligonucleotide from 20-120 nucleotides in length comprising repeats of the sequence GT;
An antisense oligonucleotide targeting any part of any HBV mRNA;
An antisense oligonucleotide targeting any part of the human apolipoprotein H mRNA;
A siRNA targeting any part of any HBV mRNA; and
A siRNA targeting any part of the human apolipoprotein H mRNA.

In another embodiment, the uses or method of treatments described above further comprise administering or using concurrently a third pharmaceutically acceptable agent selected from the following:
tenofovir disoproxil fumarate;
entecavir;
telbuvidine;
adefovir dipivoxil; and
lamivudine.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 2 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID No: 2 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 3 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 3 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 10 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 10 and a second pharmaceutically acceptable agent which comprises pegylated interferon α-2a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 2 and a second pharmaceutically acceptable agent which comprises thymosin α1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 2 and a second pharmaceutically acceptable agent which comprises thymosin α1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 3 and a second pharmaceutically acceptable agent which comprises thymosin α1.

There is also provided a method for the treatment of or the use of the following in the treatment oft hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 3 and a second pharmaceutically acceptable agent which comprises thymosin α1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 10 and a second pharmaceutically acceptable agent which comprises thymosin α1a.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 10 and a second pharmaceutically acceptable agent which comprises thymosin α1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 2 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 2 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 3 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 3 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 10 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 10 and a second pharmaceutically acceptable agent which comprises interferon α-2b.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 2 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 2 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 3 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 3 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 10 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 10 and a second pharmaceutically acceptable agent which comprises pegylated interferon λ1.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 2 and a second pharmaceutically acceptable agent which comprises GS-9620.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 2 and a second pharmaceutically acceptable agent which comprises GS-9620.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 3 and a second pharmaceutically acceptable agent which comprises GS-9620.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 3 and a second pharmaceutically acceptable agent which comprises GS-9620.

There is also provided a method for the treatment of or the use of the following in the treatment of hepatitis B infection or of hepatitis B/hepatitis D co-infection, the method or use comprising administering to a patient in need of such treatment a first pharmaceutically acceptable agent which comprises SEQ ID NO: 10 and a second pharmaceutically acceptable agent which comprises GS-9620.

There is also provided method for the treatment of or the use of the following in the treatment of hepatitis B infection or of hepatitis B/hepatitis D co-infection, the method or use comprising administering to a patient in need of such treatment a first pharmaceutically acceptable agent which comprises an oligonucleotide chelate complex of SEQ ID NO: 10 and a second pharmaceutically acceptable agent which comprises GS-9620.

BRIEF DESCRIPTION OF THE DRAWINGS

FIG. 1A depicts lead candidate compound 1a (PBHBV-001) and FIG. 1B depicts the lead candidate compound 3c (PBHBV-2-15) as identified herein.

DETAILED DESCRIPTION

Figure 1A:
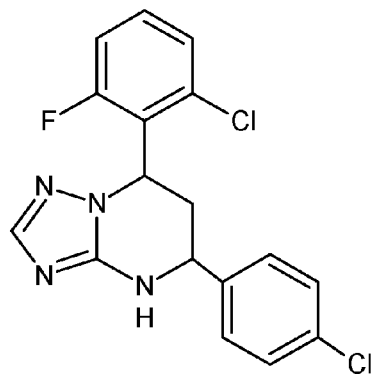
FIG. 1A and FIG. 1B illustrates the two triazolopyrimidine derivatives shown to block the release of HBsAg from the HBV producing cell line HepG2.2.15 as described in Yu et al., 2011, J. Med. Chem. 54: 5660-5670.

HBsAg plays a key role in HBV infection and HBV/HDV co-infection. Aside from its role as an essential structural component for virion formation, HBsAg is also released in large amounts into the blood of infected subjects in the form of subviral particles (SVPs), which lack the viral capsid and genome and which appear to function primarily to deliver HBsAg into the blood. SVPs are secreted from infected cells in 1,000-10,000 fold excess over virus secretion which allows SVPs to effectively sequester HBsAg antibodies (anti-HBs) so that HBV or HDV virus in the blood can escape recognition by adaptive immunity. Although several studies have also suggested that HBsAg may also function to directly block activation of adaptive and innate immune responses to HBV infection (Cheng et al., 2005, Journal of hepatology, 43:4 65-471; Op den Brouw et al., 2009, Immunology, 126: 280-289; Vanlandschoot et al., 2002, The Journal of general virology, 83: 1281-1289; Wu et al., 2009, Hepatology, 49: 1132-1140; Xu et al., 2009, Molecular immunology, 46: 2640-2646) the presence of this functionality in human HBV infection and HBV/HDV co-infection and its impact on the activity of immunotherapeutic agents has not been investigated or established. HBeAg and HBcAg have also been shown to have immunoinhibitory properties (Kanda et al. 2012 J. Inf. Dis. 206: 415-420; Lang et al. 2011 J. Hepatol. 55: 762-769; Gruffaz et al. 2013, J. Hepatol. 58 (suppl), p s155, Abstract 378).

In addition to the recognized activity of excess HBsAg in the blood (as SVPs) to sequester anti-HBs, the ability of HBsAg to block cytokine signaling in some in vitro and in vivo systems suggests that these immuno-inhibitory properties of HBsAg may also be present in HBV infection and HBV/HDV co-infection in human subjects. Due to the large excess of HBsAg in the blood of infected patients, there is likely an effective impairment of many signaling mechanisms critical for optimal immune function (both adaptive and innate). The novel disclosures presented herein further establish for the first time that many of these signaling mechanisms are also likely essential for the effects of immunotherapeutic agents to be fully realized. These disclosures also establish for the first time the critical effect of circulating HBsAg in inhibiting the action of immunotherapeutic agents.

It is provided herein the demonstration of an effective treatment against HBV infection and HBV/HDV co-infection which consists of a first pharmaceutically acceptable agent capable of removing HBsAg from the blood and an immunotherapeutic agent which stimulates immune function. Such a combination treatment allows circulating anti-HBsAg antibodies to directly attack the circulating virus and virus producing cells and, in the absence of the immuno-inhibitory properties of HBsAg, leads to a profound improvement in the effect of immunotherapy which it turn results in a much greater proportion of patients achieving immunological control of their HBV infection than with immunotherapy used alone.

Disclosed herein are novel demonstrations that, in addition to its previously described ability to block cytokine signaling in vitro, circulating HBsAg unexpectedly also directly inhibits the function of approved immunotherapies for the treatment of HBV in addition to suppressing the host immune response against HBV infection. Thus a therapy which combines a first agent capable of removing HBsAg from the blood and a second agent which stimulates immune function results in a novel synergistic action between these two agents which has a profoundly improved effect on enabling the recovery of immunological control of HBV infection.

Herein is presented data in human patients which shows that the removal of HBsAg (and other HBV antigens) from the blood of patients with chronic HBV (using nucleic acid polymers or NAPs) can allow for some measure of immunological recovery but that this level of immunological re-activation is not sufficient to generate a durable control in a large proportion of patients. This data clearly teaches that any other pharmaceutically acceptable agent or method which results in the reduction or removal of HBsAg (or in addition other HBV proteins) in the blood of infected patients will not be expected to achieve any better treatment outcome over those achieved with NAPs.

Herein is further presented data in human patients which demonstrates for the first time that the presence of HBsAg in the blood of patients with HBV infection suppresses the biochemical activity of immunotherapeutic agents like thymosin α1 or pegylated interferon α-2a. Using the NAP REP 2139, the HBsAg in the blood of patients with HBV infection was removed prior to treatment with thymosin α1 or pegylated interferon a-2α. In an HBsAg negative environment, treatment with either of these two immunotherapeutic agents resulted in a profound and unexpected synergy in activating an immunological response (as measured by production of anti-HBsAg antibodies in the blood) which was substantially stronger and occurred much more rapidly than normally observed when these immunotherapeutic agents are used in monotherapy. Most importantly, the removal of HBsAg from the blood in these patients allowed these dramatic responses to immunotherapy to occur in most patients. Any kind of positive immunological response is infrequent in patients treated with immunotherapeutic agents used in monotherapy.

These results also demonstrate for the first time that removal of HBsAg from the blood of patients with HBV infection or HBV/HDV infection will have a synergistic impact on the ability of any immunotherapeutic agent to elicit a stronger immunological response in most or all patients receiving immunotherapy with a shorter treatment regimen than typically employed. These results now clearly teach to anyone skilled in the art that any method or pharmaceutically acceptable agent which removes HBsAg from the blood of HBV or HBV/HDV co-infected patients would be expected to have the same beneficial and synergistic effect on improving the biochemical activity of any pharmaceutically acceptable immunotherapeutic agent. This improvement in the activity of the immunotherapeutic agent would be realized when the reduction or removal of HBsAg was achieved before immunotherapy or concomitantly with immunotherapy or when reduction or removal of HBsAg was achieved after immunotherapy had been previously started and continued.

The recognition of the profound synergistic antiviral effect of treating patients with a pharmaceutically acceptable agent which removes HBsAg from the blood (by any means) combined with a pharmaceutically acceptable agent which stimulates immune function represents a novel approach to achieving dramatically improved antiviral response with existing immunotherapy which was not predictable or taught in the art prior to the disclosures herein.

The term oligonucleotide (ON) refers to an oligomer or polymer of ribonucleic acid (RNA) and/or deoxyribonucleic acid (DNA). This term includes ONs composed of modified nucleobases (including 5'methylcytosine and 4'thiouracil), sugars and covalent internucleoside (backbone) linkages as well as ONs having non-naturally-occurring portions which function similarly. Such modified or substituted ONs may be preferable over native forms because of desirable properties such as, for example, reduced immunoreactivity, enhanced cellular uptake, enhanced affinity for the nucleic acid target (in the context of antisense ONs, siRNAs and shRNAs) and/or increased stability to nuclease-mediated degradation. ONs can also be double stranded. ONs also include single stranded molecules such as antisense oligonucleotides, Speigelmers and aptamers, as well as double stranded molecules such as small interfering RNAs (siRNAs) or small hairpin RNAs (shRNAs).

ONs can include various modifications, e.g., stabilizing modifications, and thus can include at least one modification in the phosphodiester linkage and/or on the sugar, and/or on the base. For example, the ON can include, without restriction, one or more modifications, or be fully modified so as to contain all linkages or sugars or bases with the recited modifications. Modified linkages can include phosphorothioate linkages, phosphorodithioate linkages, and/or methylphosphonate linkages. While modified linkages are useful, the ONs can include phosphodiester linkages. Additional useful modifications include, without restriction, modifications at the 2'-position of the sugar including 2'-O-alkyl modifications such as 2'-O-methyl modifications, 2'O-methoxyethyl (2' MOE), 2'-amino modifications, 2'-halo modifications such as 2'-fluoro; acyclic nucleotide analogs. Other 2' modifications are also known in the art and can be used such as locked nucleic acids. In particular, the ON has modified linkages throughout or has every linkage modified, e.g., phosphorothioate; has a 3'- and/or 5'-cap; includes a terminal 3'-5' linkage; the ON is or includes a concatemer consisting of two or more ON sequences joined by a linker(s). Base modifications can include 5'methylation of the cytosine base (5' methylcytosine or in the context of a nucleotide, 5' methylcytidine) and/or 4'thioation of the uracil base (4'thiouracil or in the context of a nucleotide, 4'thiouridine). Different chemically compatible modified linkages can be combined where the synthesis conditions are chemically compatible such as having an oligonucleotide with phosphorothioate linkages, a 2' ribose modification (such as 2'O-methylation) and a modified base (such as 5'methylcytosine). The ON can further be completely modified with all of these different modifications (e.g. each linkage phosphorothioated, each ribose 2' modified and each base being modified).

In the present application, the term "nucleic acid polymer" or NAP is intended to identify any single stranded ON which contains no sequence specific functionality, either to hydridize with a nucleic acid target or adopt a sequence specific secondary structure which results in binding to a specific protein. The biochemical activity of NAPs are not dependent on Toll-like receptor recognition of ONs, hybridization with a target nucleic acid or aptameric interaction requiring a specific secondary/tertiary ON structure derived from a specific order of nucleotides present. NAPs can include base and or linkage and or sugar modifications as described above. Exemplary NAP compounds include:

A phosphorothioated oligonucleotide from 20-120 nucleotides in length comprising repeats of the sequence AC;

A phosphorothioated oligonucleotide from 20-120 nucleotides in length comprising repeats of the sequence CA;

A phosphorothioated oligonucleotide from 20-120 nucleotides in length comprising repeats of the sequence TG;

A phosphorothioated oligonucleotide from 20-120 nucleotides in length comprising repeats of the sequence GT;

A phosphorothioated oligonucleotide from 20-120 nucleotides in length comprising repeats of the sequence UG;

A phosphorothioated oligonucleotide from 20-120 nucleotides in length comprising repeats of the sequence GU; and SEQ ID NOs: 1-10.

ON chelate complexes are two or more ONs linked intermolecularly by a divalent or multivalent metal cation. ON chelate complexes neutralize the inherent chelation properties of ONs which can contribute to administration—related side effects with these compounds. The administration of ON chelate complexes is a method of administering an ON to a subject where administration-related side effects associated with un-chelated ONs (which are ONs administered as sodium salts as is commonly used in the art) are mitigated. These side effects may include shivering, fever and chills with intravenous infusion or induration, inflammation and pain at the injection site with subcutaneous administration. Moreover, by preparing ONs as chelated complexes, their pharmacokinetic behavior may be improved, providing for increased therapeutic performance with similar dosing compared to un-chelated ONs as described in International application publication no. WO 2012/021985 and U.S. application publication no. 2012/0046348, which are incorporated herein by reference in their entirety. The administration of ON chelate complexes does not interfere with the biochemical activity of ONs when used normally as sodium salts. Thus any antisense ON, siRNA, or NAP as described herein can be optionally prepared as an ON chelate complex without affecting its biochemical activity.

ON chelate complexes may contain diverse multivalent metal cations including calcium, magnesium, cobalt, iron, manganese, barium, nickel, copper, zinc, cadmium, mercury and lead. It is further demonstrated that chelation of these multivalent metal cations results in the formation of ON chelate complexes comprised of two or more ONs linked via metal cations and occur with ONs greater than 6 nucleotides in length, and in the presence of ONs with either phosphodiester or phosphorothioate linkages. ONs can optionally have each linkage phosphorothioated. Chelation also occurs with ONs containing 2' modifications (such as 2'O methyl) at the ribose or containing modified bases such as 5'methylcytosine or 4-thiouracil. These 2' modifications can be present on one or more or all riboses and modified bases can be present on one or more bases or be universally present on each base (i.e. all cytosines are present as 5'methylcytosine). Additionally, the ON chelate complexes can comprise ONs which contain multiple modifications such as each linkage phosphorothioated, each ribose 2' modified and each base modified. ON modifications compatible with ON chelate complex formation are further defined above. Moreover, the chelation of the metal cations is not dependent on the sequence of nucleotides present but instead relies on the physiochemical features common to all ONs.

While the formation of ON chelate complexes can be achieved with any divalent metal cation, ON chelate complexes intended for use as medications should preferably contain only calcium and or magnesium but could also contain iron, manganese, copper or zinc in trace amounts and should not include cobalt, barium, nickel, cadmium, mercury, lead or any other divalent metal not listed here.

ONs can exert their therapeutic effects by numerous mechanisms which are either sequence dependent or sequence independent. Sequence dependent mechanisms are those which require a specific nucleic acid sequence for their activity and where the activity is reduced by one or more alterations in the nucleotide sequence present. This specific sequence may encompass the entire length of the ON or only a portion of it (a sequence motif). Examples of sequence dependent ONs include:

1. Antisense ONs either singled stranded or double stranded (e.g. synthetic interfering RNA (sRNA) or small hairpin RNA (shRNA)) are designed to target a specific region of a messanger RNA (mRNA) or a micro RNA (miRNA) of interest by a specific hybridization between the antisense ON and sequence in the targeted portion of the mRNA of interest. When antisense ONs are introduced into a cell, they result in the formation of a duplex region on the mRNA or with the miRNA which directs the degradation of this specific mRNA or miRNA by RNAse H. When siRNAs is introduced into the cell (or shRNA is expressed in the cell), the antisense strand (or guide strand) is incorporated into the RISC (RNA-induced silencing complex) which uses guide-strand targeted hybridization with the complimentary region on a target mRNA to effect its cleavage by the catylytic component of the RISC called Argonaute.

2. Stearic blocking ONs are single stranded antisense ONs which are complimentary to a specific portion of a mRNA or an immature mRNA but which are engineered to not activate RNAse H, either by containing 2' modification of every ribose, a modification known to prevent the action of RNAse H or by using modified ON chemistry (such as morpholino ONs) which is not recognized by RNAse H. The hybridization of these ONs to their target mRNAs results in a double stranded portion which provides stearic hindrance to proteins normally acting on the RNA (such as splicing proteins or ribosomes. Such ONs can be employed to block translation of a particular mRNA or to modify the post-transcriptional splicing and maturation of a particular mRNA.

3. Aptamers are ONs which adopt a specific three dimensional conformation capable of specific protein interaction and which do not readily interact with host DNA or RNA. Aptamers can also include Spiegelmers, which use L-nucleotides instead of D-nucleotides to confer high enzymatic stability to the ON.

4. Immunostimulatory ONs contain specific modifications which result in the binding to and activation of toll-like receptors 7, 8 and 9 via a non-CpG motif mediated mechanism and are capable of stimulating immune function (Kandimalla et al. 2011. Cell. Immunol. 270: 126-134; Struthers et al. 2010. Cell. Immunol. 263: 105-113).

In the design of antisense ONs, siRNAs or shRNAs, the sequence of these molecules is designed to be 100% complimentary to the intended target sequence of a specific RNA within the following guidelines:

Antisense ONs are 15-25 nucleotides in length and contain sequence which is 100% complimentary to the intended target sequence.

The guide strand of siRNA contains one oligoribonucleotide 19-21 nucleotides in length which is 100% complimentary to the targeted portion of a mRNA of interest and the passenger strand (the other strand in the duplex) contains the same length of ribonucleotide sequence which is 100% complimentary to the guide strand. Both the guide and passenger strand also have two additional deoxythymidine nucleotides on the 3' end of each strand.

shRNA molecules are produced from an expression vector such as a plasmid or viral based (e.g. lentivirus or adenovirus) expression construct which produces a long RNA which comprises the sequence of the guide and passenger strands (as described above for siRNA but which can be 19-29 nucleotides in length) in one contiguous oligonucleotide but separated by a short non-complimentary oligonucleotide sequence designed to form a hairpin. Transcription of RNA from this expression construct results in the formation of a short hairpin RNA which is processed by the dicer enzyme and loaded onto the RISC as described above for siRNA.

In the present description, the term "antiviral ON" refers to any antisense ON, siRNA, shRNA or NAP, which by virtue of its specific biochemical activity (whether sequence dependent or sequence independent) has the ability to directly or indirectly inhibit some aspect of viral replication or to directly or indirectly enhance the host's ability to clear the viral infection by immunological or other mechanisms.

In the present disclosure, the term "ON chelate complex" refers to a complex of two or more ONs in solution linked intermolecularly by a divalent metal cation as described in International application publication no. WO 2012/021985 and U.S. application publication no. 2012/0046348, which are incorporated herein by reference in their entirety. ON chelate complexes can be formed with antisense ONs, siRNA or NAPs.

In the present disclosure, the term "antiviral ON chelate complex" refers to a complex of two or more antiviral ONs in solution linked intermolecularly by a multivalent metal cation.

Phosphorothioated NAPs are a novel class of ON-based broad spectrum antiviral agents (Bernstein et al., 2008, Antimicrobial Agents and Chemotherapy, 52: 2727-2733; Cardin et al., 2009, Virology Journal, 6: 214; Guzman et al., 2007, Antiviral Therapy, 12: 1147-1156; Lee et al., 2008, Virology, 372: 107-117; Matsumura et al., 2009, Gastroenterology, 137: 673-681; Vaillant et al., 2006, Antimicrobial Agents and Chemotherapy, 50: 1393-1401 and U.S. Pat. Nos. 8,008,269, 8,008,270 and 8,067,385) which also block the formation and release of SVPs from HBV infected hepatocytes (see Example I). As SVPs constitute >99.9% of the HBsAg in the blood of patients with HBV, blockage of SVP formation and/or release from infected hepatocytes by NAPs is a highly effective method of removing HBsAg from the blood of patients infected with HBV.

As described in Example II, removal of HBsAg from the blood of infected patients by NAPs results in a partial restoration of the immune response which in turn removes HBV e-antigen (HBeAg) from the blood and substantial reduction of levels of virus in the blood during treatment but which are not maintained in most patients after treatment is stopped. While this partial restoration of the immune response (in the absence of HBsAg and other viral antigens) can lead to the establishment of durable immunological control of HBV infection after treatment is stopped in a small proportion of patients, it is not sufficient to achieve this control off treatment in the majority of patients treated. Thus the approach of simply removing HBsAg from the blood by any method or using any other pharmaceutically acceptable agent with similar effect will provide only the same moderate level of immunological recovery that will result in the establishment of durable control off treatment in a limited proportion of patients.

Figure 1B:
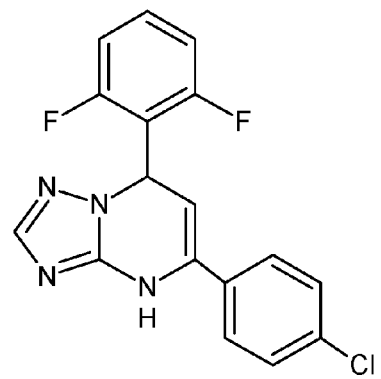

Aside from NAPs, no other agent has been publicly disclosed which has the ability to rapidly remove HBsAg from the blood in HBV infected human patients. However, there are several other methodologies which could be employed other than the use of NAPs to predictably achieve removal of HBsAg from the blood which are well known in the art. Such methodologies include (but are not limited to) the following:

A. Using a small molecule approach to target portions of the HBsAg protein or other viral or host factors involved in the formation of SVPs to block the formation of SVPs, block the transport of SVPs through the secretory machinery of the infected cell, block the release of SVPs from infected hepatocytes into the blood or generally block the release of HBsAg from infected cells. Small molecules used in this approach can include triazolopyrimidine derivatives as described in Yu et al. (2011, J. Med Chem. 54: 5660-5670) and can include the specific triazolopyrimidine derivatives as described in FIG. 1 which have been shown to block the release of HBsAg from HBV-producing cell-lines. Other small molecules can also be used which target the Apo H protein which may be important for the production of SVPs (as described in Canadian application no. 2,746,981).

B. Using an antisense based ON approach, which includes antisense oligonucleotides, siRNA or shRNA molecules to target specific mRNAs and thereby catalyze their degradation to inhibit the synthesis of HBsAg (i.e. catalyze the degradation of the mRNA which is used to produce the HBsAg protein) or other viral or host factors involved in the formation of SVPs (including Apo H as described in Canadian application no. 2,746, 981), the transport of SVPs through the secretory machinery of the infected cell or the release of SVPs from infected hepatocytes into the blood. Such an antisense based approach could also be employed to hybridize with viral or host mRNAs required for the synthesis of proteins important for the formation, intracellular transit or release of SVPs from infected hepatocytes and cause the degradation of these mRNAs by the mechanisms described above. In particular, some antisense-based approaches in HBV may be particularly advantageous as single antisense molecules such as siRNAs can be designed to interfere with all HBV mRNAs produced from the viral genome by hybridizing to a single region on the HBV genome causing the degradation of all mRNAs produced from the HBV gemone which simultaneously affects HBsAg, HBeAg and HBcAg synthesis as described in Fu et al. (2008, Acta Pharmacol. Sin. 29: 1522-1528). Two or more antisense molecules could also be used simultaneously either as separate molecules or as molecules produced from a single expression vector introduced into the infected host as described by Snyder et al. (2008, Antiviral Res., 80: 36-44). Examples known in the art for antisense-based inhibition of the synthesis of HBV proteins include:

a. Altritol-modified siRNA lipoplexes (Hean et al., 2010, Artificial DNA: PNA & XNA, 1: 17-26).
b. One or more siRNA sequences (Xin et al., 2008, World J. Gastroenterol., 14: 3849-3854; Zhe et al., 2005, J. Zhejiang Univ. Sci., 6B: 236-241 and reviewed in Chen et al., 2008, Pharmaceutical Res., 25: 72-86).
c. One or more siRNA sequences and a polyconjugate system including ARC-520.
d. Locked nucleic acid-modified antisense molecules (Sum et al., 2011, Biochem. Biophys. Res. Comm., 409: 430-435).
e. One or more shRNAs (Zhang et al., 2010, BMC Microbiol. 10:214; Starkey et al., 2009, J. Gen Virol. 90: 115-126 and reviewed in Chen et al., 2008, Pharmaceutical Res., 25: 72-86).

C. Using an ON-based aptamer approach (including classical aptamers or Spiegelmers) to target portions of the HBsAg, HBeAg or HBcAg proteins or other viral or host factors (including Apo H) present in the circulation to accelerate their removal from the blood. Classical aptamers and Spiegelmers can be further pegylated as described in Waters et al. 2011 Blood 117: 5514-5522 and Wlotzka et al. 2002 Proc. Nat. Acad. Sci. U.S.A. 99: 8898-8902 to improve their stability and circulating half-life.

D. Using an antibody based approach to directly target HBsAg and accelerate its removal from the blood.

The term "removal of HBsAg from the blood" as used herein means any statistically significant reduction of the concentration HBsAg in the blood relative to pre-treatment HBsAg blood concentrations as measured by the Abbott Architect™ quantitative HBsAg assay. This serum HBsAg assay is an accepted standard for the measurement of levels of HBsAg in the blood and is approved for diagnostic use in human patients.

Examples of ONs which can be useful in the current disclosure are provided in Table 1.

TABLE 1

Examples of ONs which can be useful in the current disclosure.

| ON class | Nucleic acid type | Sequence (5'-3') | Modifications |
|---|---|---|---|
| NAP | DNA | $(AC)_{20}$ (SEQ ID NO: 2) | All linkages PS |
| NAP | DNA | $(CA)_{20}$ (SEQ ID NO: 1) | All linkages PS |
| NAP | DNA | $(A-5'MeC)_{20}$ (SEQ ID NO: 3) | All linkages PS |
| NAP | DNA | $(5'MeC-A)_{20}$ (SEQ ID NO: 4) | All linkages PS |
| NAP | RNA | $(2'OMeA-2'OMeC)_{20}$ (SEQ ID NO: 5) | All linkages PS |
| NAP | RNA | $(2'OMeC-2'OMeA)_{20}$ (SEQ ID NO: 6) | All linkages PS |
| NAP | DNA | $(TG)_{20}$ (SEQ ID NO: 7) | All linkages PS |
| NAP | DNA | $(GT)20$ (SEQ ID NO: 8) | All linkages PS |
| NAP | RNA | $(2'OMe, 5'MeC-2'OMeA)_{20}$ (SEQ ID NO: 9) | All linkages PS |
| NAP | RNA | $(2'OMeA-2'OMe, 5'MeC)_{20}$ (SEQ ID NO: 10) | All linkages PS |
| antisense | DNA/ RNA | Sequence is 100% complimentary to a viral or host mRNA (e.g. Apo H) or to a HBV mRNA | All linkages PS, may contain a portion of RNA with 2' ribose modification or LNA |
| siRNA | Double stranded RNA/ DNA | Contains sequence 100% complimentary to a viral or host mRNA (e.g. Apo H) or to a HBV mRNA | May contain RNA with 2' ribose modification, may contain PS |
| shRNA | Double stranded RNA produced from an expression vector | Contains sequence 100% complimentary to a viral or host mRNA (e.g. Apo H) or to a HBV mRNA | RNA |

PS = phosphorothioate,
2'OMe = 2' O methyl,
5'MeC = 5'methylcytosine

Exemplary effective dosing regimens for the various pharmaceutically acceptable agents described above which can be used to achieve HBsAg removal from the blood are:
For all NAPs and phosphorothioated antisense oligonucleotides that cause the degradation of HBV or apoH mRNA, the routine use of weekly parenteral administration of 100-500 mg of compound is well established in the art to result in the achievement of therapeutically active levels of these compounds in the liver as described for NAPs in the examples below and for a phosphorothioated antisense ON causing the degradation of a liver specific mRNA (for apolipoprotein B100) by Akdim et al. 2010 Journal of the Americal College of Cardiology 55: 1611-1618).

To achieve therapeutic levels of activity in the liver, siRNAs are typically encapsulated and dosed for the specific application of degrading the mRNA for PCSK9 in the liver.

As described above, encapsulated siRNAs can achieve therapeutic effect in the liver of human patients with parenteral doses ranging from 0.015-0.20 mg/kg and are expected to be able to provide persistent effect with dosing once every two weeks or once monthly.

shRNA has not yet been used in the human setting but work in vivo in rodents has shown that expression vectors designed to express shRNA, when dosed in mice at comparable concentrations as siRNA, can be equivalently effective as siRNA (McAnuff et al. 2007. Journal of Pharmaceutical Science 96: 2922-2930. It is therefore expected that shRNA dosing, either using viral-based or encapsulartion based delivery systems as described above, achieve comparable effect in the liver with dosing regimens comparable to that used for siRNA.

Aptamers are typically pegylated to achieve improved stability and can be therapeutically effective with weekly parenteral doses of 100-600 µg/kg as described by Waters et al. 2011 Blood 117: 5514-5522.

Speiglemers are also typically pegylated to achieve an improved circulating half-life and can be therapeutically effective with parenteral doses of >1.2 mg/kg given every other day as described by Riecke et al. 2012 Abstract 2432 presented at the $54^{th}$ Annual ASH Meeting and Exposition, Atlanta, Ga., U.S.A. In the context of binding to and accelerating the removal of HBsAg or other HBV proteins from the blood of HBV-infected patients, higher doses of both aptamers or Speiglemers may be required due to the high concentrations of HBsAg typically present in patients with HBV infection.

As described above, immunotherapeutic approaches to the treatment of HBV infection have limited efficacy. One of the limitations of interferon-based monotherapy is the achievement of HBsAg removal from the blood in a very small fraction of patients (Moucari et al., 2009, Antiviral Ther., 14: 1183-1188; Reijnders et al., 2011, J. Hepatol., 54: 449-454). This HBsAg removal may underlie the achievement of durable control of HBV DNA on and off treatment in this small fraction of treated patients (Moucari et al., 2009, Hepatology, 49: 1151-1157). Another important limitation of interferon-based therapy is that it elicits only a moderate level (<50 mIU/ml) of anti-HBs production in a very small proportion of patients on treatment (Reijnders et al., 2011, J. Hepatol., 54: 449-454; Harayiannis et al., 1990, J. Hepatol., 10: 350-352) after 48 weeks of exposure. These important limitations are likely critical factors underlying the achievement of a sustained virologic response only in a limited number of patients after immunotherapy.

As described above, HBsAg can block signaling pathways important for cytokine mediated stimulation of immune function. It is well known in the art that many different classes of immunotherapeutic agents utilize several common signal transduction pathways to effect immune activation. The disclosures presented herein further show that many (or most) of these signal transduction pathways used by immunotherapeutic agents may be also blocked by the action of HBsAg. The novel disclosures herein indicate that the action of different immunotherapies are specifically inhibited by the presence of HBsAg and the therapeutic effects of these different immunotherapies, when provided in a treatment regimen, are synergistically improved in the absence of HBsAg. Therefore, removal of HBsAg from the blood would in turn result in a weaker inhibition of signaling pathways required for optimal activity of numerous different immunotherapeutic agents. Thus application of immunotherapy in patients who have previously removed HBsAg in their blood or who are actively removing HBsAg in the blood while on immunotherapy would likely experience a similar synergistic impact on the immunostimulatory effect of any immunotherapy.

In the present disclosure, the term immunotherapeutic agent refers to a small molecule or polypeptide or cytokine or hormone which by virtue of its specific biochemical activity has the ability to directly or indirectly enhance the immune function of the host. The polypeptide can be naturally derived or recombinant. The polypeptide can be recombinantly derived from a portion of the naturally occurring polypeptide. The polypeptide can be pegylated or not.

The methods for pegylation of polypeptides and the compatibility of pegylation with the biochemical activity of these polypeptides is well known in the art and consists of the linking of strands of polyethyleneglycol (PEG) to the polypeptide in question at specific amino acid residues. The primary function of pegylation is to increase the circulating lifetime of a polypeptide and also to reduce its immunogenicity. These features improve the tolerability of the polypeptide in question and reduce the frequency of dosing required for optimal therapeutic effect. It is further known in the art that the attachment of PEG residues to a polypeptide can be achieved without affecting the specific biochemical activity of the polypeptide in question. Pegylation is also known to increase the water solubility of the polypeptide in question, improving its ease of formulation. Numerous examples of pegylated polypeptides are known in the art and include: Mircera™ a pegylated form of erythropoietin; Neulasta™, a pegylated form of human granulocyte colony-stimulating factor; Pegasys™ a pegylated form of human interferon α-2a; Pegintron™, a pegylated form of human interferon α-2b; and pegylated interferon λ1 (which is currently in clinical development).

Additionally, immunotherapeutic agents which have not been previously shown to have useful immunotherapeutic activity in the presence of HBV proteins (e.g. in infected patients, chimpanzees or cellular models) may now be shown to have useful immunotherapeutic activity with the removal of HBsAg from the blood and may be further useful in the treatment of HBV in combination with any agent which removes HBsAg from the blood.

The demonstration of antiviral activity of any immunotherapeutic agent is generally accepted as an indirect measure of its ability to stimulate immune function such that this stimulated immune function has antiviral affect. Therefore, any immunotherapeutic agent with antiviral activity has an ability to stimulate immune function.

Several immunotherapeutic agents are currently approved for the treatment of viral infections which include pegylated interferon α-2a (Pegasys™) for the treatment of HBV and hepatitis C (HCV)), interferon α-2b (Intron-ATM) for the treatment of HBV and HCV) and thymosin α1 (Zadaxin™) for the treatment of HBV in most Asian countries. There are also other immunotherapeutic agents with demonstrated antiviral activity including the cytokines interferon λ1, λ2, λ3 and γ and TNFα (Friborg et al., 2013, Antimicrobial Agents and Chemotherapy, 57: 1312-1322; Lau et al. 1991, Hepatology 14: 975-979; McClary et al. 2000. Journal of Virology 74: 2255-2264; Robek et al. 2005. Journal of Virology 79: 3851-3854), pegylated interferon λ1 (Muir et al., 2010, Hepatology, 52: 822-832), and small molecule Toll-like receptor agonists like GS-9620 (currently in development by Gilead Sciences), ANA-773 (currently in development by Anadys) and the immunostimulatory oligonucleotides IMO-2055 and IMO-2125 (currently in development by Idera Pharmaceuticals) (Wu et al., 2007, Hepatology, 46: 1769-1778; Horscroft et al., 2012, J. Antimicrob. Chemotherapy, 67: 789-801). Additionally, the hormone dehydroepiandrosterone (5-androstene-3β-17-one, DHEA) and many of its metabolites (including androstenediol (5-androstene-3β-17β-diol, βAED), androstenetriol (5-androstene-3β-7β-17β triol βAET) have clear, well established immunostimulatory functionality with the capability to improve the development of a protective vaccine response against viral infections and provide direct antiviral activity against numerous viral infections in vivo (Araeno et al., 1993, J. Inf. Dis., 167: 830-840; Danenberg et al., 1995, Vaccine, 13: 1445-1448; Khorram et al., 1997, J. Gerontol. A. Biol. Sci. Med. Sci., 52: M1-M7; Loria and Padgett, 1998, Rinsho Byori, 46: 505-517; Loria, 2002, Steroids, 67: 953-966; Knoferl et al., 2003, J. Appl. Physiol., 95: 529-535; Oberbeck et al., 2007, Inten. Car Med., 33: 2207-2213; Burdnick et al., 2009, Int. Immunopharmacol., 9: 1342-1346; Hazeldine et al., 2010, J. Steroid Biochem. Mol. Biol., 120: 127-136; Schmitz et al., 2013, Med. Chem., February 15, Epub ahead of print).

The measure of stimulation of immune function as described in the current disclosures and in the context of HBV infection is most easily measured by (but not restricted to) changes in the levels of free anti-HBsAg antibodies produced in a patient receiving immunotherapy. The use of the Abbott Architect™ quantitative anti-HBsAg antibody test is a method accepted worldwide for the evaluation levels of free anti-HBsAg antibodies in the serum of patients with chronic HBV infection and the appearance of or increased production of anti-HBsAg antibodies in patients with HBV infection is an accepted surrogate measure of immune response in these patients who receive immunotherapy or HBV polymerase inhibition therapy.

There are other accepted measures of immune function which may be employed to monitor improvement of immune function in the presence of the combination treatments as described above. These measures may include increases in the transcriptional activity of interferon-response genes or increases in the levels of HBV-specific CD4+ or CD8+ T-cells in the blood or the increased levels of various cytokines in the blood such as IL2 (Liang et al. 2011. Virology Journal 8: 69).

The use of vaccination against HBV (typically using HBsAg as the antigen) is a well-recognized method for effectively preventing HBV infection and is a method adopted world-wide for the prevention of the spread of HBV infection. However, vaccination against HBV antigens has only a moderate to negligible effect in a therapeutic setting, even when the vaccine combines two different HBV antigens such as HBsAg and HBcAg (Mahtab et al. 2013. J. Hepatol. 58 (supp 1) abstract 760). According to the disclosures provided herein, this poor effect may be due to the circulating levels of HBsAg present in the blood of these patients and therefore the ability of a vaccine to stimulate the production of new antibodies to HBsAg (or to other HBV proteins) may be greatly improved with removal of HBsAg from the blood.

Thus there are many immunotherapeutic agents known to be able to stimulate immune function which may be of utility when administered before, during or after removal of HBsAg from the blood, these immunotherapeutic agents include (without restriction):

Thymosin α1;
Any α-interferon or pegylated derivatives thereof;
Any β-interferon or pegylated derivatives thereof;
Any γ-interferon or pegylated derivatives thereof;
Any λ-interferon or pegylated derivatives thereof;
Interferon α-2a or α-2b or α-N3;
Interferon β-1a or β-1b;
Interferon γ-1b;
Interferon λ1 or λ2 or λ3;
Pegylated interferon α-2a or α-2b or λ1 or λ2;
Thymic protein A;
Any antiviral cytokine or pegylated derivatives thereof;
Any polypeptide shown to have antiviral activity or immunostimulatory activity;
An immunostimulatory oligonucleotide such as IMO-2125 and IMO-2055;
A vaccine targeting any HBV antigen;
A small molecule Toll-like receptor agonist such as GS-9620, and ANA-773; and
Any hormone shown to have antiviral activity or immunostimulatory activity such as DHEA or its metabolites.

Exemplary effective dosing regimen of immunotherapeutic agents used to achieve stimulation of immune function can include:

Weekly doses of 90-180 ug in the case of Pegasys™ (according to the package insert);
Weekly doses of 3.2 mg in the case of Zadaxin™ (according to the package insert);
Weekly doses of $1 \times 10^7$ U in the case of Intron-A™ (according to the package insert);
Weekly doses of 1.5-3.0 ug/kg in the case of pegylated interferon λ1 as described in Muir et al., 2010, Hepatology, 52: 822-832;
Similar weekly doses as described above for any cytokine or immunotherapeutic peptide whether pegylated or unpegylated;
Weekly doses of 0.16-0.48 mg/kg/week for the non CpG immunostimulatory oligonucleotide IMO-2125.
Normally proscribed vaccine doses according to the convention practices in the art and specifically for the HBV vaccines Energix-B™ Recombivax-HB™.

Therefore, with the disclosures presented herein any of the above recited methods or agents capable of achieving removal of HBsAg in the blood of patients when combined with the stimulation of the host immune function by any of the immunotherapeutic agents recited above would be expected to produce a synergistic effect on the reconstitution of the immune function in patients with HBV infection or HBV/HDV co-infection. In addition to achieving the restoration of an immune function better able to sustain control of infection off treatment, such synergy could also be expected to reduce the dose of one or both agents and even the duration of treatment with either agent required to establish a therapeutically effective immune response in a majority of patients. Example III illustrates the synergistic effect on immunological recovery when removal of HBsAg by the NAP REP 2139 is followed by add-on therapy with either thymosin α1 or pegylated interferon α-2a.

In the context of combining an agent which can remove HBsAg from the blood with an immunotherapeutic agent, any amount of HBsAg removal may provide a synergistic improvement in the activity of an immunotherapy and a fractional dose of a particular immunotherapeutic agent may result in comparable or even superior immunostimulatory activity of an immunotherapeutic agent, even if HBsAg is not completely removed. Thus, combining any agent resulting in HBsAg removal from the blood with any immunotherapeutic agent will have a synergistic effect on the action of both agents which has the potential to improve the durability of the antiviral response (host immunological control) off treatment and may also require reduced doses of both agents to achieve a similar or even superior effect than when either is used in monotherapy.

Therefore, according to the disclosures presented herein, it may be useful to treat a subject with HBV infection or HBV/HDV co-infection with a pharmaceutically acceptable agent which results in the reduction of or clearance of HBsAg from the blood in combination with a second pharmaceutically acceptable immunotherapeutic agent.

It may also be useful to administer both pharmaceutically acceptable agents in the same pharmaceutical composition or to administer both pharmaceutically acceptable agents in separate pharmaceutical compositions at the same time or at different times.

It may also be useful to administer the pharmaceutically acceptable agents by the same or different routes of administration.

In order to provide the best possible antiviral response in a subject, it may be necessary to add to the combination therapies described above a HBV polymerase inhibitor such as (but are not restricted to): tenofovir disoproxil fumarate, entecavir, telbuvidine, adefovir dipivoxil or lamivudine. Such antiviral drugs can prevent the replication of the double stranded viral genome in HBV and lower the concentration of HBV virus in the blood.

The compositions described herein may be administered by any suitable means, for example, orally, such as in the form of tablets, capsules, granules or powders; sublingually; buccally; parenterally, such as by subcutaneous, intravenous, intramuscular or injection or infusion techniques (e.g., as sterile injectable aqueous or non-aqueous solutions or suspensions); by inhalation; topically, such as in the form of a cream or ointment; or rectally such as in the form of suppositories or enema; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps. Thus, the above compositions may be adapted for administration by any one of the following routes: oral ingestion, inhalation, subcutaneous injection, intramuscular injection, intraperitoneal injection, intravenous injection or infusion, or topically.

The present disclosure will be more readily understood by referring to the following examples.

Example I

NAPs Inhibit the Transit of HBsAg Out of Cells

HBsAg has been shown to block many aspects of the immune response to HBV infection (Cheng et al., 2005, J. Hepatology, 43: 465-471; Moucari et al., Hepatology 49: 1151-1157; Vanlandschoot et al., 2002, J. Gen. Virol. 83: 1281-1289; Woltman et al., 2011, PloS One 6: e15324; Wu et al., 2009, Hepatology 49: 1132-1140 and Xu et al., 2009, Mol. Immunology 46: 2640-2646). Therefore, elimination of circulating HBsAg may be a critical factor in allowing the restoration of immunocompetence in patients with chronic hepatitis B infection. An efficient method for eliminating HBsAg in the circulation is to prevent the formation and or release of subviral particles (SVPs) from infected cells (SVPs are the major carrier of HBsAg to the blood). The morphogenesis and intracellular transit of SVPs can be modeled in vitro in BHK-21 cells by expressing the small form of the HBsAg protein (sHBsAg) which is the form specifically enriched in SVPs. This model system is considered to be a surrogate model for the morphogenesis and transit of HBV SVPs (Patient et al., 2007, J. Virology 81: 3842-3851). Owing to the critical role of serum HBsAg in allowing chronicity of HBV infection, the efficacy of compounds in this model demonstrates their antiviral activity against HBV.

Various NAP compounds were tested in sHBsAg-expressing BHK-21 cells including the fully degenerate phosphorothioated NAPs REP 2006 and REP 2107, a non-phosphorothioated, fully 2'O methylated degenerate NAP (REP 2086) as well as the NAPs consisting of a poly AC sequence: REP 2055 (SEQ ID NO: 2) and REP 2148 (SEQ ID NO: 3). These NAPs were introduced into BHK-21 cells at the same time as the template RNA for sHBsAg expression using electroporation. Activity in the BHK model system was assessed by visualizing the location of HBsAg protein inside the BHK-21 cells by immunofluorescence microscopy. Formation of SVPs in the perinuclear space was visualized by transmission electron microscopy. Compounds were judged to be active if HBsAg was restricted to the perinuclear space and prevented from transiting to the periphery of the cell (secretion) or if the formation of SVPs was prevented. The activity of the various NAP compounds are summarized in Table 2 below.

TABLE 2

Effect of various NAPs on HBsAg transit in BHK-21 cells

| NAP | HBsAg retained in the perinuclear space | HBsAg transit to cellular periphery | SVP formation |
|---|---|---|---|
| control (no NAP present) | − | ++++ | ++++ |
| REP 2006 | ++++ | − | − |
| REP 2107 | +++ | + | − |
| REP 2086 | − | ++++ | ++++ |
| REP 2055 (SEQ ID NO: 2) | ++++ | − | not examined |
| REP 2148 (SEQ ID NO: 3) | ++++ | − | not examined |

− = effect not observed
+ to ++++ = marginal to complete effect observed

The results with treatment of sHBsAg expressing BHK-21 cells with REP 2006 and REP 2107 demonstrate the ability to NAPs to block formation of SVPs and the transit of sHBsAg in a sequence independent fashion. The lack of activity with REP 2086 demonstrates that these activities of NAPs are strictly dependent on the presence of phosphorothioation. Moreover, this ability was retained in the presence of 2' ribose modification (in REP 2107) and base modification (5'methylcytosine in the case of REP 2148). Additionally, REP 2107, REP 2055 are known to be completely devoid of any immunostimulatory activity and were comparably active to REP 2006. Also the defined sequence of poly AC (REP 2055 and REP 2148) was comparably active to the degenerate sequence (REP 2006 and REP 2107).

These results show that within the context of a degenerate sequence and sequences containing repeats of alternating purine/pyrimidine nucleotides such as AC (and therefore also CA) and also such as TG and GT or UG and GU and optionally comprising 2' ribose modifications and/or base modifications, NAPs will be expected to be able to block the formation of and intracellular transit and secretion of SVPs from infected cells at oligonucleotide lengths from 20-120 nucleotides according to the sequence independent properties of NAPs as described in U.S. Pat. Nos. 8,008,269B2, 8,008,270B2 and 8,067,385B2.

Example II

Effect of HBsAg Clearance from the Blood of HBV Infected Patients on Removal of Other HBV Proteins and Immunological Recovery Patients chronically infected with HBV were treated with the NAP REP 2055 (also known as REP 9AC, SEQ ID NO: 2) to remove HBsAg from their blood. The effect of REP 2055 administration (typically weekly dosing of 400 mg) on HBsAg levels in the blood was monitored using the Abbott Architect™ quantitative HBsAg test and is presented in Table 3.

TABLE 3

Effect of treatment with the NAP REP 2055 on blood levels of HBsAg in patients with chronic HBV infection.

| Patient | Pretreatment HBsAg (IU/ml) | End of treatment HBsAg (IU/ml) |
|---|---|---|
| 1 | 934 | 0.14 |
| 2 | 1885.4 | 0.38 |
| 3 | 384.1 | 0.00 |
| 4 | 126465.07 | 0.03 |
| 5 | 158180 | 0.00 |
| 6 | 36996 | 7.00 |
| 7 | 4672.5 | 43.7 |

The removal of HBsAg from the blood elicited an immunological recovery as evidenced by the additional reduction of circulating HBeAg (measured in two patients by the Abbott Architect™ quantitative HBeAg test—see Table 4), the appearance of free anti-HBsAg antibodies (as measured by the Abbott Architect™ quantitative test—see Table 5) and reduction of HBV virus in the blood (HBV DNA as measured by the Roche Cobas™ quantitative test—see Table 6). While reductions in circulating HBV virus were observed in all patients, these were of varying degrees. Moreover, the levels of free-anti-HBsAg antibody titers detected on treatment in most of these patients was moderate at best and in most cases inferior to anti-HBsAg antibody titers in the blood observed with the HBsAg vaccination of healthy non-infected adults.

TABLE 4

Effect of HBsAg clearance on HBeAg clearance.

| Patient | Pretreatment HBeAg (IU/ml*) | On treatment HBeAg (IU/ml*) |
|---|---|---|
| 1 | 1181.29 | 7.63 |
| 2 | 78.25 | 8.211 |

*measured using the Abbott Architect™ quantitative assay

TABLE 5

Effect of HBsAg clearance on the detection of free anti-HBsAg antibody in patients with chronic HBV infection.

| Patient | Pretreatment anti-HBsAg* (mIU/ml) | End of treatment anti-HBsAg* (mIU/ml) |
|---|---|---|
| 1 | 0 | 13.2 |
| 2 | 1 | 22.8 |
| 3 | 5.68 | 277 |
| 4 | 3 | 5.39 |
| 5 | 4.99 | 385.7 |
| 6 | 1 | 19.7 |
| 7 | 2 | 19.2 |

*measured using the Abbott Architect™ quantitative assay

TABLE 6

Effect of HBsAg clearance on blood levels of HBV virus (HBV DNA)

| Patient | Pretreatment HBV DNA* (copies/ml of serum) | End of treatment HBV DNA* (copies/ml of serum) |
|---|---|---|
| 1 | $2 \times 10^6$ | <500 |
| 2 | $1.4 \times 10^7$ | $1.39 \times 10^4$ |
| 3 | $4.5 \times 10^7$ | <116 |
| 4 | $1.9 \times 10^{12}$ | $3.1 \times 10^6$ |
| 5 | $7.9 \times 10^{11}$ | <116 |
| 6 | $4.8 \times 10^{11}$ | 372 |
| 7 | $1.8 \times 10^7$ | $3.5 \times 10^6$ |

*measured using the Roche Cobas™ assay

Removal of REP 2055 treatment from these patients led to the eventual long term rebound in viremia in 5/7 patients who had cleared serum HBV proteins (reappearance of HBsAg in the blood, reduction or disappearance of anti-HBsAg antibodies in the blood and rise of HBV DNA to pre-treatment levels). Thus, treatment with NAPs, or any other agent which results in the removal of HBsAg (and other HBV antigens) from the blood, will be expected to experience a similar rebound in viral activity when treatment is halted in the absence of any concomitant immunotherapy.

Example III

Combination Therapy with a NAP Chelate Complex and Two Different Immunotherapies in the Treatment of Chronic Hepatitis B in Human Patients REP 2139-Ca is the calcium chelate complex of the NAP REP 2139 (SEQ ID NO: 10) prepared in normal saline using a ratio of 30 mg of $CaCl_2$ for every 100 mg of oligonucleotide present. The preparation of REP 2139 as a calcium chelate complex is used to improve the tolerability of ON administration (see International application publication no. WO2012/021985 and U.S. application publication no. 2012/

0046348), and does not interfere with its specific antiviral activity. REP 2139-Ca (typically administered with weekly 500 mg doses) clears HBsAg from the blood (and subsequently HBeAg) and HBV virions (HBV DNA) in HBV infected patients in identical fashion to REP 2055 via the same mechanism of action (see Tables 3, 4 and 6 versus 7, 8 and 9 respectively) and therefore also demonstrates that NAPs containing both 2' ribose modifications and modified bases (e.g. REP 2139) can act to reduce HBsAg in the blood and that ONs prepared as chelate complexes (e.g. REP 2139-Ca) can be used to reduce or clear HBsAg from the blood.

TABLE 7

Effect of REP 2139-Ca monotherapy on serum HBsAg in patients with chronic HBV infection.

| Patient | serum HBsAg (mIU/ml)* | |
|---|---|---|
| | Pre-treatment | REP 2139-Ca |
| 1 | 70050 | 0.19 |
| 2 | 13400 | 0 |
| 3 | 3654.3 | 0.34 |
| 4 | 47689.7 | 180.44 |
| 5 | 107659 | 32.15 |
| 6 | 58937.87 | 9.91 |
| 7 | 17988 | 29.21 |
| 8 | 125000 | 0.01 |
| 9 | 1288.56 | 0.02 |

*measured using the Abbott Architect ™ quantitative HBsAg assay

TABLE 8

Effect of REP 2139-Ca induced HBsAg clearance on serum HBeAg levels

| Patient | serum HBeAg (index*) | |
|---|---|---|
| | Pre-treatment | REP 2139-Ca |
| 1 | 1.488 | 0.38 |
| 2 | 556.27 | 0.34 |
| 3 | 662.09 | 1.62 |
| 4 | 1100.43 | 0.31 |
| 5 | 1815.75 | 1.11 |
| 6 | 561.96 | 0.32 |
| 7 | 15.27 | 18.27 |
| 8 | 1767.85 | 0.40 |
| 9 | 101.73 | 19.35 |

*<1 = not detected, ≥1 = highly infectious state

TABLE 9

Effect of REP 2139-Ca monotherapy on serum HBV DNA (virions) in patients with chronic HBV infection.

| Patient | serum HBV (copies/ml)* | |
|---|---|---|
| | Pre-treatment | REP 2139-Ca |
| 1 | $9.89 \times 10^{8}$** | 791 |
| 2 | $1.66 \times 10^{8}$ | 1680 |
| 3 | $2.01 \times 10^{8}$ | 3643 |
| 4 | $1.28 \times 10^{8}$ | 9060 |
| 5 | $9.89 \times 10^{8}$ | $2.52 \times 10^{6}$ |
| 6 | $8.71 \times 10^{8}$ | 558 |
| 7 | $7.1 \times 10^{5}$ | $1.94 \times 10^{4}$ |
| 8 | $9.89 \times 10^{8}$ | 552 |
| 9 | $9.9 \times 10^{6}$ | 3250 |

*measured using the Roche Cobas ™™ assay
**upper limit of quantification

As described in Example II, the limitation of NAP therapy (or any therapy which can clear HBsAg) is that while the patient's current levels of anti-HBs production are "freed" to clear the virus during NAP therapy, this level of antibody production (and the removal of immuno-inhibition caused by HBsAg) in most patients is not sufficient to provide complete control of HBV infection after NAP treatment is stopped. REP 2139-mediated HBsAg clearance from the blood achieved the same general levels of anti-HBsAg antibodies in the blood as REP 2055 when used in monotherapy (see Tables 5 and 10 [end of monotherapy]) and as such would be clearly expected to result in the same poor retention of immunological control when treatment was withdrawn as was the case for the NAP REP 2055 (see Example II above). The results of NAPs used in monotherapy identifies what is a likely underlying (and previously unrecognized) defect in the ability of the immune system to regenerate a fully competent immune response to the HBV infection even in the absence of these HBV proteins, which is likely caused by chronic exposure to HBsAg, HBeAg and HBcAg causing durable immunological damage which persists in HBV-infected subjects even after these antigens are cleared from the blood.

To examine if NAP treatment (which removes HBsAg from the blood) could synergize with immunotherapy (stimulation of immune function), patients who had cleared or reduced their serum HBV proteins while on REP 2139-Ca monotherapy received either thymosin α1 (Zadaxin™—given as a 1.6 mg subcutaneous injection twice weekly) or pegylated interferon α-2a (Pegasys™—given as a 90-180 µg subcutaneous injection once weekly) as an add-on therapy to continued REP 2139-Ca administration. Pegylated interferon α-2a is sold under the trademark Pegasys™ by Roche Inc. (Basel, Switzerland) and is approved for the treatment of chronic HBV infection. Thymosin a1 is sold under the trademark Zadaxin™ by SciClone Pharmaceuticals (Foster City, Calif., U.S.A.) and is also approved for the treatment of chronic HBV infection Interferon-based monotherapy typically results in only a moderate level (<50 mIU/ml) of anti-HBsAg antibody in the blood in a very small proportion of patients (<10%) after 48 weeks of therapy (Reijnders et al., 2011, J. Hepatol., 54: 449-454; Harayiannis et al., 1990, J. Hepatol., 10: 350-352) and the antiviral effects of thymosin α1 are similarly limited (Yang et al., 2008, Antiviral Res. 77: 136-141). However, when either thymosin α1 or pegylated interferon α-2a was added to REP 2139-Ca treatment after HBsAg removal from the blood had been achieved, a profound increase in anti-HBsAg antibody levels was achieved in all patients which greatly exceeded anti-HBsAg levels observed with NAP-mediated HBsAg clearance alone or those reported for immunotherapy alone (see Table 10). Moreover, this clearly synergistic effect on increases in anti-HBsAg antibody levels was achieved with only 13 weeks of immunotherapy in combination with REP 2139-Ca (compared to a 48 week regimen usually prescribed for these immunotherapies) and also occurred in two patients with half the dose of Pegasys (90 ug) normally prescribed for the treatment of HBV. In addition, this synergistic response occurred in 9/9 (100%) of patients. The profound re-activation of anti-HBsAg production observed with the add-on immunotherapy after HBV protein removal from the blood is only one direct measure of the synergistically improved functioning of immunotherapy in the absence of HBsAg. Based on these findings, one would predict synergistically improved performance in other areas of immune stimulation such as T-cell mediated immunity and innate immunity, which may also be required to achieve complete immunological control over HBV infection.

TABLE 10

Synergistic effect on anti-HBsAg production after combination treatment with REP 2139-Ca and thymosin α1 or pegylated interferon α-2a

| Immunotherapeutic agent given in combination | Patient | serum anti-HBsAg antibody (mIU/ml)* | |
|---|---|---|---|
| | | REP 2139-Ca (end of monotherapy) | REP 2139-Ca + add-on immunotherapy** |
| Thymosin α1 | 1 | 19.36 | 987.03 |
| | 2 | 365 | 1302 |
| | 3 | 44.64 | 1108 |
| Pegylated interferon α-2a | 4*** | 5.36 | 381.57 |
| | 5*** | 2.12 | 288.85 |
| | 6 | 1.64 | 798.22 |
| | 7 | 19.69 | 223.29 |
| | 8 | 42.07 | 242.31 |
| | 9 | 42.61 | 499.05 |

*measured using Abbott Architect ™ quantitative anti-HBsAg ELISA
**13 weeks of continuous immunotherapy (add-on) after HBsAg reduction was achieved with REP 2139-Ca monotherapy.
***these two patients received 90 ug of Pegasys/week The results presented in Table 10 demonstrate that the clearance of serum HBsAg has a profound synergistic effect on the ability of either thymosin α1 or pegylated interferon α-2a to stimulate immune function which was not predicted in the art. All patients achieved very high titers of anti-HBsAg antibodies (and thus likely a more effective overall immune stimulation) with a much shorter regimen of immunotherapy than would normally be required to achieve even much lower titers of anti-HBsAg antibodies in the blood when used in monotherapy and even then only in a small fraction patients. In Table 10, all patients who had cleared serum HBsAg responded strongly to immunotherapy. In many cases, clear increases in anti-HBsAg production were detected after as little as 6-10 weeks of immunotherapy. These synergistic effects on stimulation of host immunity have led to the off treatment control of HBV infection in 8/9 patients and clearly demonstrate the synergistic impact of re-establishing a competent immune response in most patients with HBV infection when immunotherapy is given in the absence of circulating HBsAg.

These results demonstrate that any pharmaceutically acceptable agent which can reduce or clear HBsAg from the blood, when administered in combination with an immunotherapeutic agent, will have a beneficial and synergistic effect on the stimulation of immune function (such as but not limited to anti-HBsAg antibody production) in patients with chronic HBV. Example III clearly shows that removal of HBsAg from the blood synergistically improves the ability of immunotherapy to elicit a strong host derived antiviral immune response and strongly suggests that persistently circulating HBsAg in the blood of patients receiving only immunotherapy is having a profound inhibitory effect on the activity of the immunotherapy and likely underlies the poor performance of accepted immunotherapies in achieving an immunological control of infection which endures off treatment. Example III also clearly shows that the synergistic effects on the restoration of immune function occurred in all patients, who all achieved anti-HBsAg levels in the blood much more rapidly, and at much greater levels than observed with immunotherapy alone and in all cases exceeding the levels of anti-HBsAg antibodies typically observed in healthy, non-infected HBsAg vaccinated individuals. These effects could even be achieved with low doses of immunotherapy (Pegasys at 90 ug/week) which are known to be suboptimal when used in monotherapy. With HBV protein removal alone, or immunotherapy alone, these strong protective levels of anti-HBsAg antibodies are rarely observed.

The removal of serum HBsAg achieved with NAPs in the current disclosure exemplifies the best effect which could be achieved with any other agent designed to reduce or clear HBsAg (or other HBV antigens) from the blood, regardless of its mechanism of action. As such, the observations of synergy between HBsAg removal from the blood and stimulation of immune function observed using NAPs and the immunotherapeutic agents Pegasys™ and Zadaxin™ clearly demonstrate to anyone skilled in the art that the same synergistic effects with immunotherapy could now be reliably predicted to occur with the use of any agent capable of reducing or clearing HBsAg from the blood, regardless of the chemistry or mechanism of action of the agent. Therefore, the disclosures herein provide clear and novel teaching that the synergistic effects on immunological stimulation in HBV infected patients with NAPs used in combination with Zadaxin™ or Pegasys™ could be realized in HBV infection with the combinations of any agent or method able to reduce or clear HBsAg from the blood and any second agent able to stimulate immune function. The synergistic effects demonstrated with REP 2139-Ca and thymosin α1 or pegylated interferon α-2a would also be expected to occur with other combinations of agents as recited in the current disclosure where the first agent is able reduce or clear HBsAg from the blood and the second agent is able to stimulate immune function. Furthermore, it can be envisaged that combinations of two or more different agents able to reduce of clear HBsAg from the blood combined with two or more different immunotherapeutic agents may also have similar or superior effect.

While removal of HBsAg from the blood alone likely provides the large majority of the synergistic impact on immunotherapy, the additional clearance of HBeAg and HBcAg may also contribute marginally to the synergistic effect due to their intrinsic immuno-inhibitory properties. Thus the additional clearance of HBeAg and HBcAg from the blood (an effect also achieved with NAPs) may provide a minimal performance advantage but would be of little or no effect in the absence of HBsAg clearance.

The striking effect that HBsAg removal or clearance from the blood has on the effect of conventional immunotherapies may also dramatically improve the effect of vaccines to HBV antigens when administered in a therapeutic setting. From the disclosures herein, one skilled in the art would reasonably assume that circulating HBsAg was inhibiting a fully potentiated vaccine response in HBV infected subjects and further that the vaccine response would be greatly improved when administered in the absence of or reduced levels of HBsAg.

Example IV

REP 2139-Ca/Pegasys™ Combination Treatment at the Start of Therapy in Patients with Chronic Hepatitis B in Human Patients In a new cohort of HBV infected patients, REP 2139-Ca (500 mg once weekly) and Pegasys™ (180 ug weekly) were both started at the beginning of therapy to see if the synergistic effects observed in Example III could be achieved earlier in the treatment regimen. In these three patients, rapid and dramatic reductions in serum HBsAg and rapid development of free anti-HBsAg antibody titers were observed (see Table 11).

TABLE 11

Synergy of REP 2139-Ca and Pegasys ™ when combined at the start of therapy

| Patient | Serum HBsAg (U/ml*) | | Serum anti-HBsAg (mIU/ml*) | |
| --- | --- | --- | --- | --- |
| | Pre-treatment | Treatment week 9 | Pretreatment | On Treatment |
| 1 | 2510.66 | 0.17 | 0.48 | 123.75 (week 17) |
| 2 | 4789.73 | 0.02 | 0.4 | 521.57 (week 15) |
| 3 | 3338.24 | 0.05 | 0.8 | 646.42 (week 11) |

*as measured using the Abbott Architect ™ platform

The results from Example IV demonstrate that the synergy of simultaneously combining HBsAg removal from the blood with immunotherapy can occur very early on during therapy when NAPs and Pegasys™ are both started at the beginning of therapy. Further, these results and the results in Example III show that the profound improvement in the effect of immunotherapy can occur when the immunotherapy is added after HBsAg removal from the blood has been achieved or when the immunotherapy is added during the removal of HBsAg from the blood (i.e. at the start of treatment).

While Examples II, III and IV were conducted in patients with HBV monoinfection, in view of the critical and well established role HBsAg plays in HDV virus formation and immunosuppression in HBV/HDV co-infection, these examples provide clear teaching that the concepts recited in the present disclosure should be applicable to both HBV monoinfection and HBV/HDV co-infection.

The above description is meant to be exemplary only, and one skilled in the art will recognize that changes may be made to the embodiments described without departing from the scope of the invention as defined by the appended claims. Still other modifications which fall within the scope of the present invention, as defined in the appended claims, will be apparent to those skilled in the art, in light of a review of this disclosure.

What is claimed is:

1. A method for the treatment of hepatitis B infection or hepatitis B/hepatitis D co-infection, the method comprising administering to a patient in need of such treatment at least one of a first pharmaceutically acceptable agent consisting of:
   an oligonucleotide selected from the following:
      SEQ ID NOs: 1, 2, 3, 4, 5, 6, 9, 10, 11, 12, 13, 14, 15, 16, 17, 18, 19 or 20; and
      a nucleic acid polymer selected from the following:
         a phosphorothioated oligonucleotide from 20-120 nucleotides in length consisting of repeats of the sequence AC; and
         phosphorothioated oligonucleotide from 20-120 nucleotides in length consisting of repeats of the sequence CA;
   and one or more of a second pharmaceutically acceptable agent consisting of:
      thymosin α1;
      any pegylated α-interferon;
      any pegylated β-interferon;
      any pegylated γ-interferon;
      any pegylated λ-interferon;
      GS-9620 (4-amino-2-butoxy-8-[[3-(pyrrolidin-1-ylmethyl)phenyl]methyl]-5,7-dihydropteridin-6-one);
      dehydroepiandrosterone;
      androstenediol; or
      androstenetriol;
   wherein all cytosines in the oligonucleotide are present as 5'methylcytosine.

2. The method of claim 1, wherein at least one 2' ribose modification is present in the oligonucleotide.

3. The method of claim 1, wherein all riboses in the oligonucleotide have a 2' modification.

4. The method of claim 1, wherein at least one 2'O-methyl ribose modification is present in the oligonucleotide.

5. The method of claim 1, wherein all riboses in the oligonucleotide have a 2'O-methyl modification.

6. A method for the treatment of hepatitis B infection or hepatitis B/hepatitis D co-infection, the method comprising administering to a patient in need of such treatment at least one of a first pharmaceutically acceptable agent consisting of:
   an oligonucleotide selected from the following:
      SEQ NOs: 1, 2, 3, 4, 5, 6, 9, 10, 11, 12, 13, 14, 15, 16, 17, 18, 19 or 20; and
      a nucleic acid polymer selected from the following:
         a phosphorothioated oligonucleotide from 20-120 nucleotides in length consisting of repeats of the sequence AC; and
         a phosphorothioated oligonucleotide from 20-120 nucleosides in length consisting of repeats of the sequence CA;
   and one or more of a second pharmaceutically acceptable agent consisting of:
      thymosin α1;
      any pegylated α-interferon;
      any pegylated β-interferon;
      any pegylated γ-interferon;
      any pegylated λ-interferon;
      GS-9620 (4-amino-2-butoxy-8-[[3-(pyrrolidin-1-ylmethyl)phenyl]methyl]-5,7-dihydropteridin-6-one);
      dehydroepiandrosterone;
      androstenediol; or
      androstenetriol;
   wherein the oligonucleotide further comprises all riboses having the 2'O methyl modification and all cytosines present as 5'methylcytosine.

7. The method of claim 1 or 6, wherein the one or more of second pharmaceutically acceptable agent is pegylated interferon α-2a, pegylated interferon α-2b, pegylated interferon λ1, or pegylated interferon λ2.

8. The method of claim 1 or 6, wherein said first and second pharmaceutically acceptable agents are formulated within the same pharmaceutical composition.

9. The method of claim 1 or 6, where said first and second agents are formulated within separate pharmaceutical compositions.

10. The method of claim 1 or 6, wherein said first and second agents are administered simultaneously.

11. The method of claim 1 or 6, wherein said first and second agents are administered by a different route of administration.

12. The method of claim 1 or 6, wherein said first and second agents are administered using one or more of the following: oral ingestion, aerosol inhalation, subcutaneous injection, intramuscular injection, intraperitoneal injection, intravenous injection and intravenous infusion.

13. The method of claim 1 or 6, which further comprises administering a third pharmaceutically acceptable agent comprising one or more compounds selected from the following:
   tenofovir disoproxil fumarate;
   entecavir;
   telbuvidine;
   adefovir dipivoxil; and
   lamivudine.

* * * * *